(12) United States Patent
Walker et al.

(10) Patent No.: US 7,892,188 B2
(45) Date of Patent: Feb. 22, 2011

(54) METHOD AND APPARATUS FOR CHARACTERIZATION OF CLOT FORMATION

(75) Inventors: William F. Walker, Barboursville, VA (US); Michael Lawrence, Charlottesville, VA (US); Francesco Viola, Charlottesville, VA (US); Margaret D. Kramer, Carmel, IN (US)

(73) Assignee: Hemosonics, LLC, Charlottesville, VA (US)

( * ) Notice: Subject to any disclaimer, the term of this patent is extended or adjusted under 35 U.S.C. 154(b) by 1377 days.

(21) Appl. No.: 10/971,178

(22) Filed: Oct. 22, 2004

(65) Prior Publication Data

US 2005/0148899 A1  Jul. 7, 2005

Related U.S. Application Data

(60) Provisional application No. 60/513,264, filed on Oct. 22, 2003.

(51) Int. Cl.
    *A61B 5/103*  (2006.01)
    *A61B 5/117*  (2006.01)
    *A61B 5/00*   (2006.01)
    *A61B 8/00*   (2006.01)

(52) U.S. Cl. .................. 600/587; 600/368; 600/369; 600/437; 600/438; 600/552

(58) Field of Classification Search .............. 600/300, 600/368, 369, 437, 438, 442, 444, 445, 446, 600/453, 454, 455, 459, 552, 586, 587
See application file for complete search history.

(56) References Cited

U.S. PATENT DOCUMENTS

| | | | |
|---|---|---|---|
| 4,112,740 A | 9/1978 | Brandestini |
| 4,558,589 A | 12/1985 | Hemmes et al. |
| 4,705,756 A | 11/1987 | Spillert et al. |
| 4,814,247 A | 3/1989 | Spillert et al. |

(Continued)

OTHER PUBLICATIONS

Anderson, "Preventing Deep Vein Thrombosis and Pulmonary Embolism" Center for Outcomes Research, U Mass Med Center 1998, 23 pgs.

(Continued)

*Primary Examiner*—Jeffrey G Hoekstra
(74) *Attorney, Agent, or Firm*—Law Office of Alan W. Cannon

(57) ABSTRACT

Methods, apparatus and systems for characterizing changes in at least one physical property of soft tissue. A series of acoustic pulses is generated and directed into the soft tissue such that at least one of the pulses is of sufficiently high intensity to induce physical displacement of the tissue. Waves reflected off the tissue, or a flexible member that moves with the tissue, are received and measured to estimate at least one characteristic of the physical displacement induced thereby. Repetition of the generating, receiving and estimating steps provides characterization of the at least one physical property over time. Methods, apparatus and systems for characterizing at least one physical property of blood, by generating a series of acoustic pulses and directing the series of pulses into the blood such that at least one of the pulses is of sufficiently high intensity to induce physical displacement of the blood. Acoustic pulses and/or optical waves reflected from the blood, or a flexible member in contact with the blood that moves with the blood, are received and measured to estimate at least one characteristic of the physical displacement induced thereby.

33 Claims, 7 Drawing Sheets

U.S. PATENT DOCUMENTS

| | | | |
|---|---|---|---|
| 4,852,577 | A | 8/1989 | Smith et al. |
| 4,900,679 | A | 2/1990 | Spillert et al. |
| 5,056,357 | A | 10/1991 | Dymling et al. |
| 5,104,975 | A | 4/1992 | McCormick et al. |
| 5,205,159 | A | 4/1993 | Carr et al. |
| 5,234,839 | A | 8/1993 | McCormick et al. |
| 5,273,517 | A | 12/1993 | Barone et al. |
| 5,311,908 | A | 5/1994 | Barone et al. |
| 5,331,964 | A | 7/1994 | Trahey et al. |
| 5,487,387 | A | 1/1996 | Trahey et al. |
| RE35,171 | E | 3/1996 | McCormick et al. |
| 5,605,154 | A | 2/1997 | Ries et al. |
| 5,606,971 | A | 3/1997 | Sarvazyan et al. |
| 5,657,760 | A | 8/1997 | Ying et al. |
| 5,673,699 | A | 10/1997 | Trahey et al. |
| 5,744,898 | A | 4/1998 | Smith et al. |
| 5,810,731 | A | 9/1998 | Sarvazyan et al. |
| 5,854,423 | A | 12/1998 | Venegas |
| 5,921,928 | A | 7/1999 | Greenleaf et al. |
| 6,039,691 | A | 3/2000 | Walker et al. |
| 6,083,159 | A | 7/2000 | Driscoll et al. |
| 6,114,135 | A | 9/2000 | Goldstein |
| 6,135,957 | A | 10/2000 | Cohen-Bacrie et al. |
| 6,225,126 | B1 | 5/2001 | Cohen et al. |
| 6,264,609 | B1 | 7/2001 | Herrington et al. |
| 6,371,912 | B1 | 4/2002 | Nightingale et al. |
| 6,402,704 | B1 | 6/2002 | McMorrow |
| 6,508,768 | B1 | 1/2003 | Hall et al. |
| 6,537,819 | B2 | 3/2003 | Cohen et al. |
| 6,573,104 | B2 | 6/2003 | Carr et al. |
| 6,613,573 | B1 | 9/2003 | Cohen |
| 6,632,678 | B2 | 10/2003 | Aiken et al. |
| 6,692,439 | B1 | 2/2004 | Walker et al. |
| 6,716,168 | B2 | 4/2004 | Nock et al. |
| 6,764,448 | B2 | 7/2004 | Trahey et al. |
| 6,787,363 | B2 | 9/2004 | Cohen et al. |
| 6,797,519 | B2 | 9/2004 | Cohen et al. |
| 6,890,299 | B2 | 5/2005 | Cohen et al. |
| 6,951,544 | B2 | 10/2005 | Trahey et al. |
| 7,179,652 | B2 | 2/2007 | Cohen et al. |
| 7,192,726 | B1 | 3/2007 | Carr et al. |
| 7,202,048 | B2 | 4/2007 | Carr, Jr. |
| 7,207,939 | B2 | 4/2007 | Husher |
| 7,261,861 | B2 | 8/2007 | Kautzky |
| 7,374,538 | B2 | 5/2008 | Nightingale et al. |
| 7,399,637 | B2 | 7/2008 | Wright et al. |
| 7,422,905 | B2 | 9/2008 | Clague et al. |
| 7,439,069 | B2 | 10/2008 | Nippoldt et al. |
| 7,524,670 | B2 | 4/2009 | Cohen et al. |
| 7,732,213 | B2 | 6/2010 | Cohen et al. |
| 2003/0171676 | A1 | 9/2003 | Trahey et al. |
| 2003/0204141 | A1 | 10/2003 | Nock et al. |
| 2004/0068184 | A1 | 4/2004 | Trahey et al. |
| 2004/0167403 | A1 | 8/2004 | Nightingale et al. |
| 2005/0004463 | A1 | 1/2005 | Chen et al. |
| 2005/0015001 | A1 | 1/2005 | Lee et al. |
| 2007/0038095 | A1 | 2/2007 | Greenleaf et al. |
| 2007/0184508 | A1 | 8/2007 | Cohen et al. |
| 2008/0038828 | A1 | 2/2008 | Cohen et al. |
| 2008/0249408 | A1 | 10/2008 | Palmeri et al. |
| 2009/0112483 | A1 | 4/2009 | Cohen |

OTHER PUBLICATIONS

Beer: Center for Reproductive Immunology & Genetics, "Thrombophilia: Inherited and Acquired," 6 pgs. http://repro-med.net/papers/thromb.php.

Bilgen, et al. "Error analysis in acoustic elastography. II. Strain estimation and SNR analysis," Journal of the Acoustical Society of America, vol. 101, 1997, pp. 1147-1154.

Bercoff et al. "In vivo breast tumor detection using transient elastography," Ultrasound in Medicine & Biology, vol. 29, 2003, pp. 1387-1396.

Chaturvedi, et al. "Testing the limitations of 2-D companding for strain imaging using phantoms," IEEE Transactions on Ultrasonics Ferroelectrics & Frequency Control, vol. 45, 1998, pp. 1022-1031.

Cohn et al. "An elasticity microscope. Part I: Methods," IEEE Transactions on Ultrasonics Ferroelectrics & Frequency Control, vol. 44, 1997, pp. 1304-1319.

Cohn et al. "An elasticity microscope. Part II: Experimental Results" vol. 44, 1997, pp. 1320-1331.

Emelianov et al. "Ultrasound Elasticity Imaging of Deep Venous Thrombosis," 2000, pp. 1791-1794.

Freedman, et al. "A Meta-Analysis of Thromboembolic Prophylaxis Following Elective Total Hip Arthroplasty," Journal of Bone and Joint Surgery, vol. 82-A, 2000, pp. 929-938.

Fatemi et al. "Ultrasound-Stimulated Vibro-Acoustic Spectrography," vol. 280, 1998, pp. 82-85.

Fatemi et al. "C-Scan Imaging by Radiation Force Stimulated Acoustic Emission Method," Proc. IEEE Ultrasonics Symp., 1996, pp. 1459-1462.

Fertner et al. "Comparison of Various Time Delay Estimation Methods by Computer Simulatoin," vol. 34, 1986, 1329-1330.

Gauss et al., "Adaptive Imaging in the Thyroid Using Fundamental and Harmonic Echo Data," presented at IEEE Ultrasonics Symposium, 1999, pp. 1515-1519.

Gauss et al. "Wavefront Estimation in the Human Breast," presented at SPIE Medical Imaging, vol. 4325, 2001, pp. 172-180.

Harris et al. "Evaluation of recurrent thrombosis and hypercoagulability" American Family Physician, vol. 56, 1997, 6 pgs.

Hirsh et al, "Management of deep vein thrombosis and pulmonary embolism. A statement for healthcare professionals. Council on Thrombosis (in consultation with the Council on Cardiovascular Radiology), American Heart Association" vol. 93, 1996, 55 pgs.

Hirsh et al. "How we diagnose and treat deep vein thrombosis," Blood, vol. 99, 2002, pp. 3102-3110.

Jensen et al. "Calculation of pressure fields from arbitrarily shaped, apodized, and excited ultrasound transducers," IEEE Transactions on Ultrasonics, Ferroelectrics, and Frequency Control, vol. 39, pp. 1992, 262-267.

Lerner et al. "Sono-elasticity: medical elasticity images derived from ultrasound signals in mechanically vibrated targets," vol. 16, 1988, pp. 317-327.

Lubinski et al. "Adaptive strain estimation using retrospective processing medical US elasticity imaging," IEEE Transactions on Ultrasonics Ferroelectrics & Frequency Control, vol. 46, 1999, pp. 97-107.

McAleavey et al. "Estimates of echo correlation and measurement bias in acoustic radiation force impulse imaging," IEEE Transactions on Ultrasonics Ferroelectrics & Frequency Control, vol. 50, 2003, pp. 631-641.

Nightingale et al. "Acoustic remote palpation: initial in vivo results," presented at IEEE Ultrasonics Symposium, 2000, pp. 1553-1558.

Nightingale et al. "Acoustic Radiation Force Impulse Imaging: In Vivo Demonstration of Clinical Feasibility," Ultrasound in Medicine & Biology, vol. 28, 2002, pp. 227-235.

O'Donnell et al. "Internal Displacement and Strain Imaging using Ultrasonic Speckle Tracking," IEEE Transactions on Ultrasonics, Ferroelectrics and Frequency Control, vol. 41, 1994, pp. 314-325.

Ophir et al. "Elastography: A Quantitative Method for Imaging the Elasticity of Biological Tissues," vol. 13, 1991, pp. 111-134.

Parsons, et al. "Age Determination of Experimental Venous Thrombi by Ultrasonic Tissue Characterization," Journal of Vascular Surgery, vol. 17, 1993, 470-478.

Rubin et al., "Clinical application of sonographic elasticity imaging for aging of deep venous thrombosis: preliminary findings," Journal of Ultrasound in Medicine, vol. 22, 2003, pp. 443-448.

Sugimoto et al. "Tissue Hardness Measurement Using the Radiation Force of Focused Ultrasound," Proc. IEEE Ultrason. Symp., 1990, pp. 1377-1380.

Shung et al. "Ultrasonic characterization of blood during coagulation," Journal of Clinical Ultrasound, vol. 12, 1984, pp. 147-153.

Sarvazyan et al. "Shear Wave Elasticity Imaging—A New Ultrasonic Technology of Medical Diagnostics," Ultrasound in Medicine and Biology, vol. 24, 1998, pp. 1419-1436.

Torr, "The Acoustic Radiation Force," Am. J. Phys., vol. 52, 1984, pp. 402-408.

Viola et al. "A comparison of the performance of time-delay estimators in medical ultrasound," IEEE Transactions on Ultrasonics Ferroelectrics & Frequency Control, vol. 50, 2003, pp. 392-401.

Viola et al. "Sonorheometry: A Noncontact Method for the Dynamic Assessment of Thrombosis," The Annals of Biomedical Engineering, vol. 32, 2004, pp. 696-705.

Viola et al. "Ultrasound echo decorrelation due to acoustic radiation force," vol. 2, 2002, pp. 1903-1906.

Viola et al. "Radiation Force Imaging of Viscoelastic Properties with Reduce Artifacts," vol. 50, 2003, pp. 736-742.

Viola et al. "Comparison of Time Delay Estimators in Medical Ultrasound," 2001, pp. 1485-1488.

Viola et al. "A Spline Based Algorithm for Continuous Time Delay Estimation Using Sampled Data," IEEE Transactions on Ultrasonics Ferroelectrics & Frequency Control, in press. 56 pgs.

Viola et al. "Imaging Viscoelastic Properties of the Vitreous" 2001, pp. 1623-1626.

Viola et al. "Efficient and Accurate Spline-Based Time Delay Estimation" 4 pgs.

Viola et al. "Analysis of Clot Formation with Acoustic Radiation Force" 8 pgs.

Walker, et al. "A Fundamental Limit on the Accuracy of Speckle Signal Alignment," 1994, pp. 1787-1791.

Walker et al. "A Method of Imaging Viscoelastic Parameters with Acoustic Radiation Force," vol. 45, 2000, pp. 1437-1447.

Walker et al. "A Fundamental Limit on Delay Estimation Using Partially Correlated Speckle Signals," IEEE Transactions on Ultrasonics, Ferroelectrics and Frequency Control, vol. 42, 1995, pp. 301-308.

Walker et al. "Real-Time Imaging of Tissue Vibration Using a Two-Dimensional Speckle Tracking System," IEEE Ultrason. Symp., 1993, pp. 873-877.

Walker et al. "Applications of Acoustic Radiation Force in Ophthalmic Ultrasound," Proc. IEEE Ultrason. Symp., vol. 2, 1997, pp. 1291-1295.

Walker et al. "The Significance of Correlation in Ultrasound Signal Processing," 2001, 13 pgs.

Webster, Medical Instrumentation: Application and Design. New York: John Wiley & Sons, 1998, 6 pgs.

Hartley et al., Characteristics of Acoustic Streaming Created and Measured by Pulsed Doppler Ultrasound. pp. 1278-1285, vol. 44, No. 6, Nov. 1997.

Hartley., Doppler Measurement of Acoustic Streaming. pp. 1537-1540, 1995.

Quantitative Investigation of Acoustic Streaming in Blood, pp. 1110-1121, J. Acoust. Soc. Am.111, Feb. 2002.

Sakharov et al., Acceleration of Fibrinolysis by High-Frequency Ultrasound: The Contribution of Acoustic Streaming and Temperature Rise. pp. 333-340, 2000.

Shi et al., Experimental Investigation and Finite Element Simulation of Streaming in Blood in Cylindrical Models. pp. 1509-1512, 2000.

Shi et al., Color Doppler imaging of acoustic streaming in blood and clot. pp. 1315-1318, 1999.

Shi et al., Color Doppler Detection of Acoustic Streaming in a Hematoma Model. pp. 1255-1264, vol. 27, No. 9, 2001.

Viola et al., Analysis of Clot Formation with Acoustic Radiation Force. pp. 235-242 & pp. 1-2, vol. 4689, 2002.

Nightingale, et al., Shear-Wave Generation Using Acoustic Radiation Force: In Vivo and EX Vivo Results. vol. 29, No. 12, pp. 1715-1723, 2003.

METHOD AND APPARATUS FOR CHARACTERIZATION OF CLOT FORMATION

CROSS-REFERENCE

This application claims the benefit of U.S. Provisional Application No. 60/513,264, filed Oct. 22, 2003, which application is incorporated herein, in its entirety, by reference thereto.

GOVERNMENT RIGHTS

This invention was made with government support under federal grant no. GAAN P200A010433 awarded by the Department of Education. The United States Government may have certain rights in this invention.

BACKGROUND OF THE INVENTION

Blood coagulation is a delicately regulated process that serves as a protective mechanism against blood loss due to tissue damage. Overactive or unregulated coagulation can lead to conditions including myocardial infarction, stroke, deep vein thrombosis (DVT), and pulmonary embolism. The ability to recognize coagulation disorders and quantify their severity is critical for identifying those at risk and implementing appropriate prophylactic treatment. Because of inherent risks accompanying anticoagulant therapy, such as hemorrhage or anaphylaxis, it is critical that such therapies be prescribed appropriately (see Anderson et al., "Best Practices: Preventing Deep Vein Thrombosis and Pulmonary Embolism", Center for Outcomes Research, U. Mass. Med. Ctr, 1998.

Hypercoagulability, or thrombophilia, is an inherited or acquired coagulation disorder in which there is either an overactivation of coagulation or deficient deactivation of developed thrombus. While a number of factors within the coagulation cascade such as factor V Leiden, protein C or S deficiency, and antithrombin III deficiency are known to increase the propensity to clot (see Harris et al. "Evaluation of Recurrent Thrombosis and Hypercoagulability", American Family Physician, vol. 56 (6), Oct. 15, 1997, there is currently a dearth of techniques available to quantify these effects clinically. The methods currently available are mostly biochemical in nature and test for a specific genetic mutation or abnormal chemical reaction rate, such as Leiden Factor V. mutation R560Q; Hyperhomocysteinemia MTHFR Mutation; Prothrombin Gene Mutation 20210; Protein C levels; Protein S levels; Activated Protein C activity; antibodies to six phospholipids of the IgM, IgG and IgA classes; Lupus anticoagulant antibody; Russell Viper Venom time; Activated Partial Thromboplastin time; and Prothrombin time. While these tests may provide valuable information, they are unable to determine the coagulation rate of an individual's blood. Furthermore, since the coagulation cascade is exceedingly complex, there are numerous steps in the pathway that might be disrupted or inappropriately regulated. However, it is not always possible to determine if these interruptions in the cascade are predictive of an observable clinical impact on thrombus formation.

Mechanical methods, such as cone and plate viscometry or indentation testing, provide the most intuitive way to characterize the mechanical parameters of blood coagulation. However, these approaches are limited because the mechanical forces applied to the forming thrombus can disrupt its delicate structure, and thus disturb the system enough to interrupt the normal course of coagulation.

Deep vein thrombosis (DVT) refers to the formation of a blood clot in a large vein of the leg. DVT often results from a lack of movement in the extremities for significant periods of time or from an increased propensity to clot due to malignancy, recent surgery or trauma, pregnancy, hormonal agents such as oral contraceptives, or other contributing causes, see Hirsh et al., "How We Diagnose and Treat Deep Vein Thrombosis", Blood, vol. 99(1), pp. 3102-3110. If a portion of the thrombus breaks off and travels to the pulmonary vessels, a potentially fatal pulmonary embolism can result. Clinical diagnosis cannot serve as the sole means of DVT diagnosis because many potentially dangerous venous thrombi are asymptomatic, and many of the symptoms are not unique to DVT. Current noninvasive methods of diagnosis such as duplex ultrasonography, venography, impedance plethysmography, and MRI can often detect the presence of a clot, but are limited by an inability to determine the stage of development of the clot so identified. Furthermore, these methods must often be used in conjunction with another diagnostic method or tool such as the d-dimer assay in order to make a conclusive diagnosis.

Although duplex ultrasonography is favored for the initial investigation of DVT, several groups have also proposed the use of ultrasound to extrapolate parameters related to the formation of DVT. Shung et al, in "Ultrasonic Characterization of Blood During Coagulation", Journal of Clinical Ultrasound, vol. 12, pp 147-153, 1984, have shown that the increase in echogenicity associated with the formation of a thrombus is mostly due to an increase in ultrasonic backscatter. They have also found increases in both the attenuation coefficient and the speed of sound. Parsons et al. in "Age Determination of Experimental Venous Thrombi by Ultrasonic Tissue Characterization", Journal of Vascular Surgery, vol. 17(3), pp. 470-478, 1993 (which is hereby incorporated herein, in its entirety, by reference thereto), have been able to differentiate in vivo between clots of varying ages by looking a the slope and intercept of the linear fit of the normalized power spectrum. Emelianov et al., in "Ultrasound Elasticity Imaging of Deep Vein Thrombosis" Proc. IEEE Ultrasonic Symposium, 2000 (which is hereby incorporated herein, in its entirety, by reference thereto), have characterized different clinical stages of a thrombus using maps of local strain. Their method operates by obtaining baseline radio frequency (RF) echo data, mechanically compressing the tissue, obtaining a second compressed set of data, and applying signal processing methods to create maps of local strain. Rubin et al., in "Clinical application of sonographic elasticity imaging for aging of deep venous thrombosis: preliminary findings," Journal of Ultrasound in Medicine, vol. 22, pp. 443-8, 2003, which is incorporated herein, in its entirety, by reference thereto, characterizes different clinical stage of a thrombus using maps of local strain obtained by compressive elastography. Although the techniques proposed by Parsons et al., Emelianov et al. and Rubin et al. have yielded valuable results, they are primarily focused on age classification of DVT and thus are not able to characterize thrombus formation. Furthermore, these techniques do not provide information about coagulability and are thus of little or no value in prospectively identifying patients at high risk of forming a blood clot. Furthermore, direct translation of these techniques to benchtop tools is problematic because of high variability in measurements taken.

There remains a need for the ability to characterize changes in soft tissue, and particularly for characterizing thrombus formation. There remain needs for methods, apparatus and systems that can characterize thrombus formation for diagnosis and treatment purposes, and preferably in a substantially non-invasive manner.

SUMMARY OF THE INVENTION

The present invention provides methods of characterizing at least one physical property of soft tissue. One such method described herein includes generating a series of acoustic pulses and directing them into the soft tissue to be characterized, wherein at least one of the pulses is of sufficiently high intensity to induce physical displacement of the tissue. At least one physical property of the tissue is estimated based on measurement of at least two of the pulses as reflected from the soft tissue and/or receiving optical reflections from the soft tissue as the soft tissue is being physically displaced. The process may be repeated at least once after passage of a time interval, so that time-based data can be generated.

An apparatus for identifying changes in at least one physical parameter of a soft tissue over time includes an acoustic wave generator capable of repeatedly generating acoustic pulses of sufficient intensity to induce measurable physical displacement in the soft tissue; a sensor adapted to sense at least one of optical waves or the acoustic pulses after reflection by the soft tissue; a clock governing cycles during which the acoustic pulses are generated and during which sensing of at least one of the acoustic or optical waves is carried out; and a processor that receives input from the sensor and clock and calculates time-based data characterizing at least one characteristic of the physical displacement induced.

A method of characterizing at least one physical property of blood is described, including generating a series of acoustic pulses and directing the series of pulses into the blood such that at least one of the pulses is of sufficiently high intensity to induce physical displacement of the blood; measuring a displacement of the blood resulting from the induced physical displacement thereof; and estimating at least one characteristic of the physical displacement based on the measurement.

Methods of diagnosis of the development stages of clotting are described.

Methods of evaluating effectiveness of anti-clotting treatments are described.

Methods of evaluating effectiveness of pro-clotting treatments are also described.

These and other advantages and features of the invention will become apparent to those persons skilled in the art upon reading the details of the methods, apparatus and systems as more fully described below.

DETAILED DESCRIPTION OF THE INVENTION

Figure 1A:
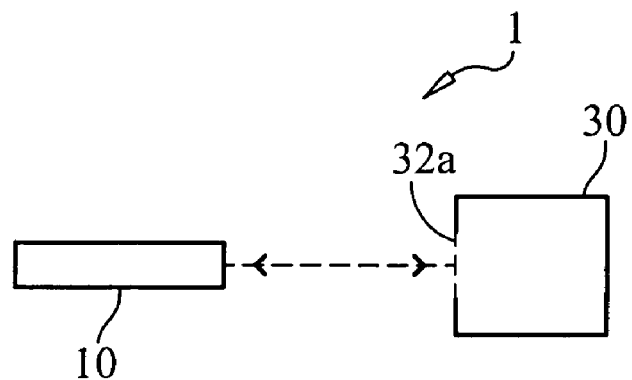
FIG. 1A is a schematic representation of the present invention useful for in vitro characterization of a soft tissue sample.

Before the present methods, apparatus and systems are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a transducer" includes a plurality of such transducers and reference to "the curve" includes reference to one or more curves and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention provides methods, apparatus and systems for performing what the present inventors have termed sonorheometry. Sonorheometry provides data about the mechanical properties of soft tissue. Furthermore, repeated measurements using sonorheometry enable characterization of changing properties over time. Sonorheometry is particularly well-suited to characterizing blood coagulation. The present invention provides data about the mechanical properties of a developing thrombus without disrupting its formation. The methods and techniques may be non-invasive or carried out in a laboratory setting after obtaining a sample from a patient, and are based on the application of acoustic radiation force to the tissue to be characterized.

An increased or decreased propensity to clot can be evaluated by observing the coagulation rate and mechanical characteristics of the developing thrombus at any time during formation. This information may in turn allow clinicians to assess an individual's clotting behavior and to treat coagulation disorders appropriately. This information may also be used to evaluate whether a particular treatment and/or dosage is effective or needs to be changed, as subsequent testing according to the present methods (i.e., after a treatment has been administered) can be carried out to compare the results, thereby indicating the effect of the treatment.

Referring now to FIG. 1, an assembly 1 is schematically shown that is set up for testing soft tissue according to the present invention. An acoustic wave generating device 10 is positioned in alignment with container 30 to allow device 10 to irradiate a soft tissue contained within container 30. Device 10 may be mounted or fixed at a predetermined distance for the contents of the container 30 to receive focused acoustical waves from device 10. Thus, device 10 and container 30 are oriented to align the emission of acoustic waves from device 10 with a sample contained in container 30. Container 30 may be entirely acoustically transparent, or contains at least one window 32a that is acoustically transparent and that is aligned with the emission pathway of device 10. As one non-limiting example, container 30 may include a plastic cuvette having windows 32a32d cut therethrough and covered with KAPTON® (polyimide) film or other acoustically transparent film. One knowledgeable in the art will realize that it may be advantageous to place the acoustic window or windows of the sample container at some non-perpendicular angle relative to the direction of wave propagation so as to reduce the magnitude of received echoes from the interfaces with the window(s). Multiple measurements may be performed at the same time using an array of sample containers 30, for example. One knowledgeable in the art will recognize that such an array may either consist of individual containers, or a single container with multiple sample compartments. Additionally or alternatively, an array of transducers may be included in device 10, or an array of devices 10 may be used to make multiple measurements. Thus, for example, multiple transducers and/or multiple devices 10 may be provided to analyze multiple samples in parallel, wherein the multiple samples are contained in multiple individual containers or a single container with multiple sample compartments.

Assembly 1 may be submerged in a tank of water or other coupling medium to facilitate transmission of the acoustic waves. Alternatively, device 10 (or other acoustic emitter and receiver) may be placed in direct contact with the sample. Still further, device 10 may be adapted to deposit the sample directly in contact therewith, for example placing a drop (or other quantity) of blood on a transducer contained in device 10 or other application feature of device 10. In the case where a bath (of water or other coupling medium) is provided, the bath may be a constant temperature bath or other means may be provided to maintain a constant sample temperature. In cases where no bath is used, it may be advantageous to place the sample in contact with a material of controlled temperature, so as to control the sample temperature. Another alternative is the use of device 10 invasively. For example, device 10 may be inserted intravascularly and delivered to the location of a stent to characterize any clotting that may be occurring as well as characterize the progression or stage of a clot that may be present. Similar intravascular techniques can be applied for identifying and/or characterizing clot processes with regard to DVT, as well as for other clotting events throughout the body, as long as the location is accessible by catheter or other delivery instrument, for example. Thus, not only are intravascular insertions, deliveries or locations made possible by the device, but the device may also be positioned at an intracavity location or other location inside of the body.

Device 10 includes an acoustic wave generating source capable of generating one or more pulses, at least one of which is of sufficient intensity to induce measurable physical displacement in the soft tissue contained in container 30. For example, device 10 may include one or more piezoelectric transducers capable of generating ultrasonic waves. Alternatively, device 10 may utilize an electric circuit to generate rapid heating and thereby generate acoustic energy. Further alternatives may be employed for generating acoustic energy, including, but not limited to: an ultrasonic generator fabricated using microelectromechanical systems (MEMS); a capacitive micromachined ultrasound transducer; a laser used to heat a target material thereby generating acoustic energy, where the laser may be targeted on a permanent component of the assembly, or on a surface of the sample, for example. Still further alternatively, a transducer may be incorporated into the sample container 30 in lieu of providing it in the device 10, as in a case, for example, where a polymer transducer material such as PVDF may be glued right onto the surface of the sample container 30.

Device 10 further includes at least one sensor capable of measuring displacement or deformation induced by the acoustic waves as they are applied to the soft tissue sample and reflected by the soft tissue sample back to device 10. In this configuration, an ultrasound sensor may be used to track the motion of the sample as induced by at least one ultrasonic wave of sufficient intensity to induce displacement of the tissue. Alternatively, tracking of the motion may be accomplished by means other than sensing reflected acoustic waves. For example, optical coherence tomography, a focused light interferometer or laser Doppler may be used to optically sense the displacement of the tissue induced by the one or more ultrasonic waves. Device 10 may include one or more sensors for carrying out any of these optical methods or such sensors may be provided in equipment that is separate from device 10. Likewise, for acoustic sensing, the one or more sensors may be one and the same as the acoustic wave generator, or may be a separate component(s) and may take any of the forms described above with regard to the acoustic wave generating component. Typically, an ultrasonic transducer may be used to both apply ultrasonic waves to the soft tissue as well as to sense ultrasonic waves reflected back from the tissue. An adjoining processor (not shown in FIG. 1) may be provided to control the timing of transmission of pulses and of receiving of echoes (reflected pulses) by device 10.

Figure 1B:
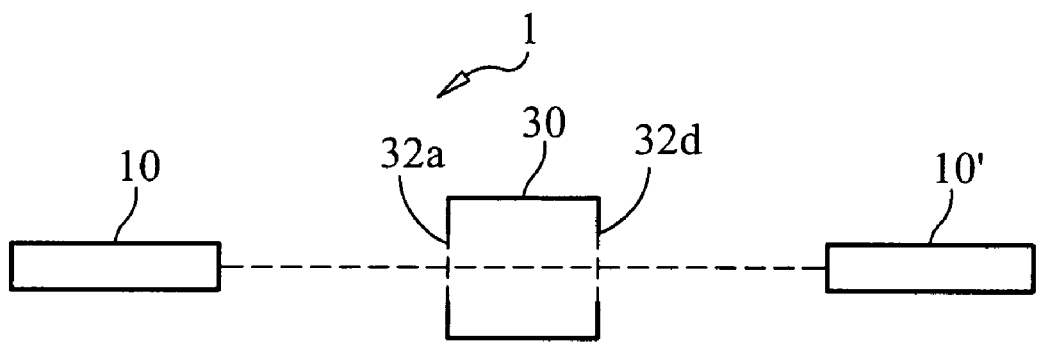
FIG. 1B is a modification of the arrangement shown in FIG. 1A in which an additional device is positioned on a side of the container opposite the device that is also shown in FIG. 1A.

FIG. 1B shows an example wherein a second device 10' is positioned in alignment with device 10, but on the opposite side of container 30 compared to the location of device 10. In this example, container 30 may be entirely acoustically transparent, or contain at least two windows 32a and 32d that are acoustically transparent and that are aligned with the emission pathway of device 10 to permit emissions to pass through both windows 32a and 32d to be received by device 10'. System 1 shown in FIG. 1B, in addition to performing the measurements that the system of FIG. 1A performs, can also measure acoustic properties, including speed of sound and attenuation, which provide indirect measures of tissue microstructure and which may be used for calibration purposes.

According to Torr, "The Acoustic Radiation Force": Am. J. Phys., vol. 52, pp. 402-408, 1984, acoustic radiation force arises from two sources: "a non zero time-averaged sound pressure in the ultrasonic beam, and the momentum transported by the beam." Torr argues, and it has been widely accepted, that the momentum transfer component of this force dominates under most conditions. This momentum transfer results from attenuation of the propagating ultrasound beam via both absorption and scattering. For the case of total absorption the applied radiation force is simply:

$$F = W/c \qquad (1)$$

where W is the acoustic power and c is the speed of sound in the medium. In the case of perfect reflection this radiation force is doubled. In both cases radiation force acts along the direction of wave propagation.

Torr discloses that the physical origin of the radiation force exerted by an ultrasonic beam on an absorbing target is explained. It is shown that the force may have two sources-a nonzero time-averaged sound pressure in the ultrasonic beam, and the momentum transported by the beam—but that there is a movement of material out of the ultrasonic beam to prevent a nonzero time-averaged sound pressure from being established. Consequently, the transfer of wave momentum is the sole cause of the force. The assumptions made in evolving this explanation are discussed, and the resulting change in mean density within the ultrasonic beam is considered. It is pointed out that the acoustic radiation force is but one example of a universal phenomenon associated with all forms of wave motion.

Introduction

Physicists are familiar with the fact that when a beam of light is absorbed or reflected by a surface a small unidirectional force is exerted on that surface; this force is said to be due to the electromagnetic "radiation pressure." However, it is not so widely appreciated that this is but one example of a universal phenomenon: All forms of wave motion, including electromagnetic waves transverse waves on an elastic string, surface waves on a liquid, and longitudinal sound waves (and even gravitational waves?) exert some kind of unidirectional radiation force on absorbing and reflecting obstacles in their path. The radiation force exerted by sound waves was first measured by Altberg in 1903. Only in recent years, however has it become of practical importance. The power outputs of the ultrasonic transducers of medical ultrasonic equipment are commonly determined by measuring the radiation force exerted by the ultrasonic beam generated by the transducer. The transducer is submerged in a tank of water and the ultrasonic beam is directed towards an absorbing or reflecting target in the tank. An absorbing target may be realized by a slab of natural rubber, or a reflecting target by an air-backed thin metal plate. If the ultrasonic beam is directed horizontally, the force can be determined by suspending the target as a pendulum and measuring its deflection. The measurements are made in water because the characteristic acoustic impedances of water and human soft tissue are similar, thus the measured ultrasonic beam power is virtually equal to the power radiated by the transducer into the human body.

It is generally accepted that the radiation force F exerted on a totally absorbing target by an ultrasonic beam of power W is given by the equation $$F = W/c, \qquad (1t)$$

where c is the speed of sound in the medium surrounding the target; for normal incidence on a plane reflecting surface the radiation force has twice this value. The speed of sound in water is 1500 ms$^{-1}$, thus the radiation force on an absorbing target in water is about $7 \times 10^{-4}$ N W$^{-1}$.

However, this equation is deceptively simple, for the theory behind it is involved and has been the subject of intermittent debate since the early considerations of Rayleigh and Brillouin. Many papers have been written on the theory, but unfortunately the majority of these are heavily mathematical and do not make clear the physical origin of the radiation force. Even those physicists who have made radiation force measurements of ultrasonic power may not understand fully how the force arises. The aim of this paper is therefore to analyze the theory, to point out the assumptions made, and to explain the physical significance of the mathematical terms which arise in the theory. The theoretical approach adopted here is based chiefly on the work of Hertz and Mende, Beyer, Borgnis, and Rooney and Nyborg. The mathematical aspects of the theory have recently been discussed more fully by Livett et al. and Chu and Apfel.

An Analysis of the Radiation Force

A parallel beam of plane waves of power W and cross-sectional area A propagates through a lossless liquid medium of density $\rho$ and is incident on a totally absorbing target. A radiation force F is exerted on the target but, following Rooney and Nyborg, it will be assumed that a constraint force $-F$ is applied to the target to prevent it from moving. If the target is suspended like a pendulum, the constraint force will be the horizontal component of the tension in the suspension. The problem is to find the magnitude of the constraint force and hence of the radiation force. The problem will be treated by using Euler's momentum theorem. The theorem is essentially Newton's second law of motion applied, not to a solid body, but to the material within a fixed region of space within a moving fluid. It is stated as follows.

Consider the fluid which at an instant t occupies the region of space bounded by the fixed closed surface S. According to Newton's second law of motion the total force acting on this mass of fluid is equal to the rate of change of momentum of the fluid. More explicitly, the resultant of the normal pressure thrusts on the surface S plus the resultant of the body forces acting on the enclosed fluid is equal to the rate of change of momentum of the enclosed fluid plus the rate of flow of momentum outwards through S.

To apply the theorem to the system described herein, the fixed surface S is drawn so that it just encloses the target. The region bounded by S is referred to as the control volume. The constraint force is exerted in a direction parallel to the direction of propagation of the ultrasonic beam, and so to determine its magnitude it is necessary only to consider forces and transfers of momentum in this direction. At any instant t the relevant forces and rates of change of momenta in the system are as follows.

The hydrostatic pressure in the liquid acts equally but in opposite directions through the left- and right-hand faces of the surface S and so exerts no net force on the material within S; it may therefore be disregarded. However, in the ultrasonic beam the sound pressure superimposed on the hydrostatic pressure exerts a force through the left-hand face of the surface S. Denoting the sound pressure in the beam at the surface S by p, the force is given by pA.

The only significant body force acting on the material within the control volume is the constraint force $-F$ acting on the target.

The rate of change of momentum $\partial M/\partial t$ of the material within the control volume is made up of the rate of change of momentum of the target and the rate of change of momentum of the small quantity of liquid in the control volume.

Lastly, associated with the propagation of the ultrasonic beam through the surface S, there is a movement of the liquid medium backwards and forwards through S and therefore a transport of momentum through S. Denoting the particle velocity in the beam at the surface S by u, the momentum per unit volume of liquid at the surface is $\rho u$, and the rate of flow of momentum inwards through unit area of the surface is $\rho u^2$. The rate of flow of momentum into the control volume is therefore $\rho u^2 A$.

Thus, from Euler's momentum theorem, $$pA = F = \frac{\partial M}{\partial t} = \rho u^2 A. \tag{2t}$$

Equation (2t) describes the instantaneous balance between the forces and rates of change of momenta in the system, and each term may be expected to be varying at the ultrasonic frequency. However, the target is so massive that it cannot respond to such rapid changes in the forces acting upon it. The quantity to be determined is the constraint force $-F$, but what is strictly required is the steady constraint force $-\overline{F}$ which, on time-average, is required to keep the target stationary. (A bar over a quantity will be used to indicate a time-averaged value.) Equation (1) is therefore averaged with respect to time. The term $\partial M/\partial t$ represents the rate of change of momentum of the target plus the rate of change of momentum of the liquid in the control volume. The target is assumed to be at rest on time-average and the presence of the solid target precludes any time-averaged movement of liquid within the control volume in the direction of propagation of the ultrasonic beam. Therefore $\overline{\partial M/\partial t}=0$.

Consequently $$-\overline{F} = -(\overline{p} + \overline{\rho u^2})A, \tag{3t}$$

and so the radiation force is given by $$\overline{F} = (\overline{p} + \overline{\rho u^2})A. \tag{4t}$$

III. Langevin Radiation Force

Equation (4t) shows that the radiation force exerted on an absorbing target has two possible origins. First, there may be a nonzero mean sound pressure $\overline{p}$ in the ultrasonic beam, giving rise to a force $\overline{p}A$ on the target. Second, the ultrasonic beam delivers momentum to the target at a rate $\rho u^2 A$ per unit time, which is revealed as a force $\overline{\rho u^2} A$. At first sight it may seem surprising that the possibility of a nonzero mean sound pressure in the ultrasonic beam is contemplated, for if the beam were being generated by a pistonlike source undergoing a sinusoidally varying displacement, it might be thought that the sound pressure in the beam at the surface S would also be varying sinusoidally and that its mean value would be zero. However, the radiation force per unit area exerted by an ultrasonic beam of intensity 1 W cm$^{-2}$ would be explained in full by the existence in the beam of a mean sound pressure $\overline{p}$ of just $10^{-4}$ times the amplitude of the sound pressure, and it will be seen in Sec. V that, to this precision, a sinusoidally oscillating piston does not generate a purely sinusoidally varying sound pressure at a point in the ultrasonic beam, even for the simplest model of the medium of propagation.

Initially, it is also difficult to accept that momentum is transported by the ultrasonic beam. It appears that the forwards and backwards movement of the layer of liquid in the beam at the surface S merely transfers momentum into and out of the control volume, giving a time-averaged momentum transfer of zero. However, as the layer of liquid moves forward through the surface S, matter enters the control volume carrying with it momentum in the direction of propagation of the beam (positive momentum), while as the layer of liquid moves backward through the surface S, matter leaves the control volume carrying with it momentum in the opposite direction (negative momentum). The removal of negative momentum from the material within the control volume is equivalent to the addition of positive momentum. Thus the momentum $\rho u^2 A$ is transferred per unit time in one direction only, and indeed $\rho u^2 A$ is clearly always positive.

All the same, it still cannot be doubted that the movement of liquid through the surface S is symmetrical, and by defining momentum to be positive in the opposite direction one can equally argue that the flow of momentum is directed away from the target. The explanation of this paradox is that although, according to this description, the direction of momentum flow is reversed, a transport of momentum from the target to the source would give rise, by reaction, to a force on the target away from the source, thus the physical consequence is the same.

Since the source, the target, and the intervening medium constitute a closed mechanical system, it follows that the source experiences a radiation force in a direction opposite to the direction of propagation of the ultrasonic beam, and this may be proven directly by applying Euler's momentum theorem to a control volume containing the source. Brillouin pointed out that effectively there is a time-averaged stress in the medium between the source and the target, forcing the two apart. He also showed that, like any other stress, this radiation stress can be concisely represented using tensor notation.

If this analysis is accepted, one is left with the problem of calculating the magnitude of the mean sound pressure $\overline{p}$ in the ultrasonic beam. It will be seen in Sec. V that the calculation of $\overline{p}$ is not a simple matter and that the value obtained for $\overline{p}$ is dependent on assumptions made about the mechanical properties of the liquid medium of propagation. However, consider the likely physical effect of a nonzero mean sound pressure in the ultrasonic beam. Under these circumstances there would, on time-average, be a pressure gradient between the liquid inside the beam and the undisturbed liquid outside. It seems likely that this would result in a movement of liquid either out of or into the beam (depending on the sign of $\overline{p}$) to bring the mean pressure in the beam to equal that in the surrounding medium. The effect would be to reduce $\overline{p}$ to zero and to cause a slight decrease or increase in the time-averaged density of the liquid inside the ultrasonic beam.

Assuming that $\overline{p}$ is thus annulled, Eq. (4t) becomes $$\overline{F} = \overline{\rho u^2} A. \tag{5t}$$

However $$\overline{E_k} = \overline{\rho u^2}/2 \tag{6t}$$

where $\overline{E_k}$ is the mean kinetic energy density in the ultrasonic beam. If $\overline{E_k}$ is taken to be equal to the mean potential energy density $\overline{E_p}$ in the beam (and this assumption is questioned in Sec. VI), then $$\overline{E_k} = \overline{E_p} = \overline{E}/2, \tag{7t}$$

where $\overline{E}$ is the mean total energy density in the beam. The radiation force may therefore be expressed as $$\overline{F} = \overline{E} A \tag{8t}$$

Alternatively this equation may be written as $$\overline{P} = \overline{F}/A = \overline{E}, \quad (9t)$$

where $\overline{P}$ is commonly referred to as the radiation pressure exerted by the ultrasonic beam. However $\overline{P}$ is not a pressure in the sense of a hydrostatic pressure and is better referred to as the radiation force per unit area.

Finally, the mean total energy density $\overline{E}$ is related to the ultrasonic beam power W by $$\overline{E} = W/cA, \quad (10t)$$

where c is the speed of sound in the liquid medium of propagation. Thus $$\overline{F} = W/c, \quad (11t)$$

which is the required relationship between the radiation force F and the beam power W, for an absorbing target.

The equation relating the radiation force exerted on a reflecting surface to the ultrasonic beam power may be derived most simply by considering the balance of forces In a closed system consisting of a source of ultrasound, a reflecting surface, and an absorbing surface. However, this approach does not reveal the origin of the force and for a physical description paralleling the one above for an absorbing target the reader is referred to Borgnis.

It should be mentioned that reflecting targets, in the form of small solid spheres a few wavelengths in diameter, are also used for the measurement of ultrasonic intensity. In this case the relationship between radiation force and energy density in Eq. (8t) is assumed and the problem is one of determining the distribution of energy density In the incident and scattered waves around the target and integrating the energy density over the surface of the target to obtain the net force.

IV. Rayleigh Radiation Force

The radiation force operating in the physical system described above has come to be known as the Langevin radiation force. However, this system is not the one examined by Rayleigh in the papers which began the study of this subject. Rayleigh considered the force exerted on one end of a fluid-filled closed cylinder by plane sound waves reflected back and forth inside the cylinder. Under these conditions it is not possible for a nonzero mean sound pressure in the cylinder to be eliminated by a movement of material out of or into the sound beam. Instead, both terms on the right-hand side of Eq. (4t) contribute to the radiation force, which is known in this case as the Rayleigh radiation force. It will be seen in Sec. V that the value of the mean sound pressure $\overline{p}$ in the cylinder is dependent on the assumed relationship between pressure and density in the fluid medium; the magnitude of the Rayleigh radiation force is therefore also dependent on this relationship.

The Rayleigh radiation force has no major practical importance. It is mentioned here only because it is invariably discussed alongside the Langevin radiation force in the theoretical literature.

V. Mean Sound Pressure in the Ultrasonic Beam

Although in deriving an expression for the Langevin radiation force it is ultimately assumed that the mean sound pressure $\overline{p}$ in the ultrasonic beam is zero, a knowledge of the mean sound pressure in the absence of any movement of material out of or into the beam does allow the calculation of the change in mean density required inside the beam to maintain $\overline{p}$ equal to zero. For this reason, and because the discussion illustrates well the difference between the so-called Lagrangian and Eulerian descriptions of an acoustical wave motion, a summary will be given of the method used to determine $\overline{p}$ First, the relationship between the sound pressure $p_L$ within, and the density $\rho_L$ of, a mass element of the liquid medium is approximated by the truncated power series $$p_L = A[(\rho_L - \rho_0)/\rho_0] + B[(\rho_L - \rho_0)/\rho_0]^2/2, \quad (12t)$$

where A and B are constants and $\rho_0$ is the density of the undisturbed medium. The subscript L is intended to indicate that $p_L$ and $\rho_L$ are Lagrangian variables, meaning that they refer to a moving mass element of liquid and not to a fixed point in space. (The importance of this distinction will soon be seen.) The constants A and B can in practice be chosen to fit closely any real medium, and the ratio B/A is known as the nonlinearity parameter of the medium.

The propagation of plane waves in the x direction through this medium is described by the Lagrangian wave equation $$\frac{\partial^2 \xi}{\partial t^2} \left[ c_0^2 \bigg/ \left(1 + \frac{\partial \xi}{\partial a}\right)^{B/A+2} \right] \frac{\partial^2 \xi}{\partial a^2}, \quad (13t)$$

where $$c_0^2 = \left(\frac{\partial p_L}{\partial \rho_L}\right)_{\rho_L = \rho_0}. \quad (14t)$$

The Lagrangian wave equation relates the displacement $\xi$ of a mass element of the medium to its rest position, a, on the x axis, and the solution of the wave equation gives the form of the displacement $\xi(a,t)$. Knowing $\xi(a,t)$ one can use the equation of motion $$\frac{\partial p_L}{\partial a} = -\rho_0 \frac{\partial^2 \xi}{\partial t^2} \quad (15t)$$

for a mass element of the medium to derive an expression for $p_L(a,t)$.

However, what is actually required is not $p_L(a,t)$, the sound pressure within a moving mass element of the medium, but the pressure at a fixed point in space. In particular, the sound pressure is required as a function of time at the fixed surface S of the control volume. This sound pressure will be denoted by $p_E(X,t)$ where the subscript E indicates that $p_E$ is an Eulerian variable, meaning that it refers to a fixed point x in space which may be occupied by different mass elements of the medium at different times.

The difference between the functions $p_L$ and $p_E$ is normally very small. This is apparent when one recognizes that the ratio of the particle displacement amplitude $\xi_0$ to the wavelength of the ultrasound is about $10^{-5}$ for an ultrasonic beam of intensity 1 W cm$^{-2}$ in water. Therefore the distinction between the Lagrangian and Eulerian variables describing the wave motion is usually of no significance because the basic behavior of sound waves undergoing, say, reflection or diffraction can be explained in terms of first-order approximations to the variables p, u, etc. However, the radiation force is influenced by second-order quantities such as $\rho u^2 A$ (here A is the cross-sectional area of the ultrasonic beam and not the constant A) and at this level of precision the difference between $p_L$ and $p_E$ is significant, as will be seen.

The solutions of the Lagrangian wave equation [Eq. (13t)] are dependent on the nonlinearity parameter B/A. For most real liquids, B/A lies between 2 and 10, and for water at 20° C. B/A=5.0. In general it is only possible to obtain approximate solutions to the wave equation, and the solutions are dependent on distance from the source of the sound; this dependence explains the progressive distortion of finite amplitude sound waves. However, it can be seen from Eq. (13t) that there are two conditions under which the wave equation is simplified. The first is $\partial\xi/\partial a \ll 1$, in which case the equation becomes $$\frac{\partial^2 \xi}{\partial t^2} = c_0^2 \frac{\partial^2 \xi}{\partial a^2}. \qquad (16t)$$

This is the small amplitude approximation which has the simple sinusoidal solutions for $\xi(a,t)$ familiar in elementary acoustics. The second condition is B/A=−2 which also produces the above equation, but in this case the sinusoidal solutions are exact for waves of arbitrary amplitude. From Eq. (15t), $p_L(a,t)$ is then also a purely sinusoidal function. So, for the special, though unrealistic, case of a medium for which B/A=−2, a sinusoidally oscillating piston source generates waves which propagate without change, irrespective of the wave amplitude.

Hertz and Mende, Beyer, and Borgnis illustrated their descriptions of the origin of the Langevin radiation force by reference to a medium of constant compressibility K, where $$K = \frac{\rho_0}{\rho_L^2} \frac{\partial \rho_L}{\partial p_L}, \qquad (17t)$$

and it may be shown (see Appendix) that such a medium represents the special case B/A=−2. Although unrealistic, this example offers the clearest illustration of how the small difference between the Lagrangian and Eulerian sound pressures $p_L$ and $p_E$ gives rise to a nonzero mean sound pressure $\bar{p}_E$ at a point in the ultrasonic beam. It is therefore worth considering this example before moving on to the general case.

For a medium of constant compressibility, a sinusoidally varying Lagrangian sound pressure $p_L(a,t)$ plotted as a function of the rest positions, a, of the mass elements of the medium. Also shown is the Eulerian sound pressure $p_E(x,t)$ plotted as a function of position x in space. It can be seen that because at any instant most of the particles in the ultrasonic beam are displaced from their rest positions the Eulerian pressure is not a simple sine wave. The compressed half-cycles of the wave are in fact slightly shorter than the rarified half-cycles, and as a result the Eulerian pressure averaged over a wavelength, and therefore the time-averaged Eulerian pressure $\bar{p}_E$ at a point in space, are slightly negative.

Hertz and Mende, Beyer, and Borgnis prove quite straightforwardly that, for a medium of constant compressibility, $\bar{p}_E = \rho u^2 = \bar{E}$. Thus from Eq. (4t) it can be seen that, but for the postulated movement of material into the ultrasonic beam from the surrounding undisturbed medium, the Langevin radiation force exerted on a target in a medium of constant compressibility would be zero.

However, from a practical point of view it is of greater interest to determine $\bar{p}_E$ for a liquid having an arbitrary value of B/A, and Westervelt, Borgnis, Hunt, Rooney and Nyborg; and Beyer1 have attempted this more difficult problem. Westervelt, Borgnis, Hunt, and Beyer used the same approach (the first three authors in fact considered the case of an ideal gas having an arbitrary value of γ, the ratio of the specific heats, but their theory is paralleled by that for a liquid having an arbitrary value of B/A) and obtained the result $$\bar{p}_E = (B/2A - 1)\bar{E}/2. \qquad (18t)$$

For B/A=−2 this equation reduces to $\bar{p}_E = -\bar{E}$ and is therefore consistent with the theory for a liquid of constant compressibility. Rooney and Nyborg used a different approach and in calculating the Rayleigh radiation force exerted on an absorbing surface they found $$\bar{p}_E = B\bar{E}/2A. \qquad (19t)$$

Again this equation reduces to $\bar{p}_E = -\bar{E}$ for B/A=−2. However Liven et al. and Chu and Apfel have pointed out an error in Rooney and Nyborg's theory. And while there is no direct experimental evidence in support of Eq. (18t), Westervelt and Borgnis also obtained an expression for the time- and space-averaged Eulerian sound pressure $\langle p_E \rangle$ in a plane standing wave which is supported directly by measurements made by Mathiot. Thus Eq. (18t) is indicated as the correct expression for $\bar{p}_E$ in a plane progressive wave.

If the value B/A=5.0 for water is entered in Eq. (18t) it is found that $\bar{p}_k = 0.75\bar{E}$. Thus the time-averaged Eulerian sound pressure in water, unlike that in a medium of constant compressibility, is positive, and it may tentatively be concluded that in water, and indeed in any other real liquid, there is a movement of material out of the ultrasonic beam to maintain $\bar{p}_E = 0$. Consequently, there is a decrease in the mean density of the medium within the beam.

From Eq. (14t), the fractional change in mean density is, to a good approximation, equal to $$\bar{p}_E / \rho_0 c_0^2. \qquad (20t)$$

For an ultrasonic beam of intensity 1 W cm$^{-2}$ in water; the mean energy density $\bar{E}$ is approximately 7 J m$^{-3}$, and the predicted fractional change in mean density within the beam is $-2 \times 10^{-9}$. The change in mean density is therefore extremely small and is dwarfed by the much larger fractional variations in density (of the order of $\pm 10^{-4}$ at the ultrasonic frequency. The movement of material out of a sound beam under the action of the sound beam appears never to have been detected, probably for this reason. This postulated movement of material is, however, vital to the theory of the Langevin radiation force and its detection and measurement would be a valuable test of the theory.

Finally, it should be mentioned that Rooney has measured the Langevin radiation force exerted by an ultrasonic beam on an absorbing target in various liquids having different values of the nonlinearity parameter B/A. In support of Eq. (11t) he found that the force was proportional to $c^{-1}$ and displayed no dependence on B/A.

VI. A Remaining Theoretical Problem: the Equality of the Mean Kinetic and Potential Energy Densities In moving from Eq. (5t) to Eq. (8t) it was necessary to assume that the mean kinetic energy density $\bar{E}_k$ and the mean potential energy density $\bar{E}_p$ in a plane progressive wave are equal. This assumption is often made in simple acoustical theory but its validity for a real liquid medium having an arbitrary value of the nonlinearity parameter B/A has been questioned.

Goldberg has stated that this assumption is "impossible in general" and has derived two expressions for the ratio $\bar{E}_p/\bar{E}_k$, one of which refers to the Eulerian energy densities and the other to the Lagrangian energy densities: both are dependent on B/A. (In fact, he considered a plane wave in a gas having an arbitrary value of γ, but the work is equally applicable to a liquid if one substitutes γ=B/A+1.) Both expressions reduce to unity for the special case B/A=−2, but for water (B/A=5.0) they equal 0.42 and 0.75, respectively.

This important question still appears to be unresolved. References to several other papers on the subject may be found in Goldberg's paper.

VII. General Approaches to the Theory

At the beginning of this paper it was stated that every type of wave motion exerts some kind of radiation force on an absorbing or reflecting obstacle in its path and invariably it is found that the radiation force per unit area is simply related to the energy density in the wave. The theory presented here has been directed specifically towards explaining the radiation force exerted by sound waves, but because similar theoretical relationships exist between radiation force per unit area and energy density for other types of wave one is led to wonder whether there exists a more abstract approach to the theory which is capable of explaining the radiation force as a universal phenomenon.

One of the earliest general approaches to the theory was made by Larmor. He calculated the radiation force exerted by a wave train on a reflecting surface and used the device of making the reflector move towards the wave source so that the energy density in the reflected wave was increased by the Doppler effect. He equated the increase in the power of the reflected wave to the rate at which work was done by the reflector in moving against the radiation force. He then let the velocity of the reflector tend to zero and found that the radiation force per unit area was equal to twice the total energy density in the incident wave train. He assumed that for an absorbing surface the radiation force would be halved.

Later, Brillouin used the Boltzmann-Ehrenfest formula (an extension of Lagrange's principle of least action) to calculate the radiation force exerted on the perfectly reflecting ends of a fluid-filled cylindrical cavity by a standing wave within the cavity. This was the problem considered by Rayleigh, and Brillouin obtained the same result as Rayleigh. The theory was applicable to both sound waves and electromagnetic waves.

Recently, Joyce has attempted a comprehensive theoretical treatment of the (radiation) forces exerted by beams of both waves and particles, and the reader is referred to his papers for a fascinating discussion.

There are, however, few other examples of attempts to bring all radiation force phenomena under the umbrella of a single theory, and the radiation forces exerted by electromagnetic waves, sound waves, and surface waves on liquids have, in the past, been studied more or less independently. Only Brillouin's name appears in treatments of both the acoustic and electromagnetic radiation forces.

Appendix: Proof that the Nonlinearity Parameter B/A is Equal to −2 for a Medium of Constant Compressibility In Sec. V it was stated that for a medium of constant compressibility K, where $$\frac{1}{K} = \frac{\rho_L^2}{\rho_0} \frac{\partial p_L}{\partial \rho_L}, \qquad (21t)$$

the nonlinearity parameter B/A is equal to −2. Although I have not seen this demonstrated explicitly in the literature, it may be proven as follows.

Differentiation of Eq. (12t) gives $$\frac{\partial p_L}{\partial \rho_L} = \frac{A}{\rho_0}\left[1 + B\left(\frac{\rho_L}{\rho_0} - 1\right)/A\right]. \qquad (22t)$$

This expression may be substituted in Eq. (21t) to obtain $$\frac{1}{K} = A\left[1 + \left(\frac{\rho_L}{\rho_0} - 1\right)\right]^2\left[1 + B\left(\frac{\rho_L}{\rho_0} - 1\right)/A\right]. \qquad (23t)$$

Expanding the right-hand side of this equation and discarding terms in $(\rho_1/\rho_0 - 1)$ of second order and above one obtains $$\frac{1}{K} = A\left[1 + \left(\frac{B}{A} + 2\right)\left(\frac{\rho_L}{\rho_0} - 1\right)\right]. \qquad (24t)$$

It can now be seen that K is constant, and therefore independent of $\rho_L$ if and only if B/A=−2.

In biological media absorption and reflection are neither total, nor isolated at interfaces. Rather, attenuation and reflection (in the form of scattering) occur throughout volumes of tissue. In these cases radiation force acts as a body force, with the force on a given volume simply equal to the sum of the force from absorption and that from scattering. If we assume that scattering in the tissue consists purely of backscatter, which is of course overly simplistic, then the radiation force applied to a given volume of tissue is:

$$F = \frac{W_a}{c} + \frac{2W_s}{c} \qquad (2)$$

where $W_a$ is the absorbed ultrasound power and $W_s$ is the scattered ultrasound power within the volume. If we further simplify by recognizing that only a fraction of the scattered energy is returned as backscatter, and that attenuation is dominated by absorption rather than scattering, then (2) can be simplified as:

$$F = \frac{W_a}{c} = \frac{A}{c}I_0(e^{-2afz_1} - e^{-2afz_2}) \qquad (3)$$

where A is the cross sectional area of the volume of interest (perpendicular to the axis of propagation), $I_0$ is the ultrasound intensity that would be observed in the absence of attenuation, α is the amplitude attenuation coefficient in Nepers per centimeter per MHz, f is the ultrasonic center frequency in MHz, and $z_1$ and $z_2$ are the ranges of the front and back of the volume in units of centimeters.

By utilizing two devices 10 and 10' (wherein device 10 at least contains an emitter and device 10' contains at least a sensor for receiving the waves/pulses that pass through windows 32a, 32d the system can also measure the waves that pass from device 10 to device 10' and estimate acoustic properties of the sample being analyzed. Examples of acoustic properties that may be estimated include attenuation, scattering, and speed of sound during sonorheometry procedures. The data received by device 10' may be used to make predictions/estimations of the applied radiation force and compare experimentally determined displacements to predicted displacements.

Figure 1C:
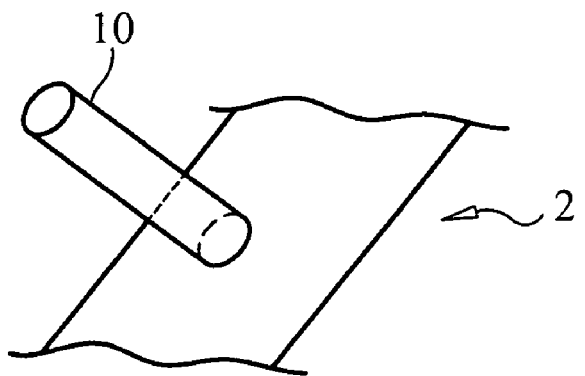
FIG. 1C schematically illustrates a non-invasive use of the present invention.

It should be noted that although FIG. 1A shows an example of apparatus for performing analysis in vitro (such as in a laboratory setting, or from a self-operated testing kit, for example) after taking a sample to be analyzed from a patient and depositing it in container 30, alternatively, the present invention may also be practiced non-invasively, such as by applying acoustic waves from a device 10 transdermally through a patient 2 (in vivo) to the targeted tissue to be analyzed, see FIG. 1C. A single time frame analysis of one or more physical properties of the tissue may be made, or time series studies may be performed by applying the waves transdermally at different time periods, using the techniques described herein for the in vitro studies. Of course the in vivo analyses would typically not involve administration of thrombin or other coagulant to a patient. However time studies may be done to test the effectiveness of an anti-clotting treatment regimen for example. Similarly, time studies may be done to test the effectiveness of a pro-clotting regimen given to a patient to increase the ability of the blood to clot, such as in the case of a hemophiliac, for example. Likewise, the administration of thrombin is not necessarily required for time studies in vitro, as there are other techniques that may be substituted to initiate coagulation, such as snake venom, the use of ground glass to initiate coagulation, etc.

Non-invasive applications of the current invention include characterizing a stage of development of a blood clot by generating a series of acoustic pulses and transdermally directing the series of pulses into the blood such that at least one of the pulses are of sufficiently high intensity to induce physical displacement of the blood, receiving at least two pulses, including at least one pulse reflected from the blood to establish a baseline and another pulse reflected from the blood to estimate at least one characteristic of the physical displacement induced by the waves. Alternatively, the at least two pulses identified above as being used for establishing baseline and estimating a characteristic resulting from the physical displacement of the sample, do not necessarily have to be reflected from the blood/sample. For example, if the sample is contained within membranes that move with the movement of the blood/sample or in a container 30 that is sufficiently flexible (such as a membranous container, for example) to move with the movements of the blood/sample, then the at least two pulses could alternatively be those reflected from the surfaces of the flexible sample container or other membranes placed within the sample, as the movement of the sample (e.g., development of the clot) will alter the position of the surfaces or membranes.

The at least one estimate may be compared to previously generated data to gauge the stage of development of the blood clot being analyzed. The previously generated data may be reference data, such as generated across a larger number of patients and then averaged to determine normal characteristics, as well as to find average levels for characterizing different stages of clotting for example. Optionally, one or more algorithms, techniques or statistical processes may be applied to the at least one estimate to correct for attenuation, scatter and/or other variables before making comparisons to the previously generated data and/or database. Additionally, or alternatively, the prior data or previously generated data may be data generated from one or more previous applications of the present invention to the same patient for the same tissue at prior times. This approach may be used to develop a history, to show the progression of the development of the clot for example. Of course, the in vitro apparatus described herein could be used to carry out the same tests outside of the body, such as in a laboratory or a patient's home test kit.

Still further evaluation of the effectiveness of an anti-clotting treatment may be performed, such as by evaluating the blood prior to application of the treatment by generating a series of acoustic pulses and directing the series of pulses into the blood such that at least one of the pulses is of sufficiently high intensity to induce physical displacement of the blood, receiving at least two pulses reflected from the blood to establish a baseline and to estimate at least one characteristic of the physical displacement induced by the waves, and then repeating these steps at least one time after administration of the treatment Of course, as noted earlier, alternative sensing or receiving steps may be taken to track the movement of the blood, such as by using any of the alternative sensing techniques described above, e.g., laser Doppler, optical coherence tomography, etc. Repeated applications of the steps at predetermined time intervals may be performed if needed to ensure a stabilization of the properties measured, as a result of the treatment. Alternatively, the analysis may indicate that a larger or smaller dose of treatment is needed, or that the treatment is ineffective for a particular patient.

Alternatively, evaluation of the effectiveness of an anti-clotting treatment may be performed by carrying out the analysis steps a number of times after treatment, at predetermined time periods after the administration of the treatment, for example. The results generated from each iteration can then be compared and analyzed to note any changes in the at least one physical characteristic that is being measured/estimated.

Maintenance monitoring can be carried out by the same techniques noted, wherein a patient can be periodically tested to ensure that a clot has not progressed further and/or is dissolving.

Figure 2:
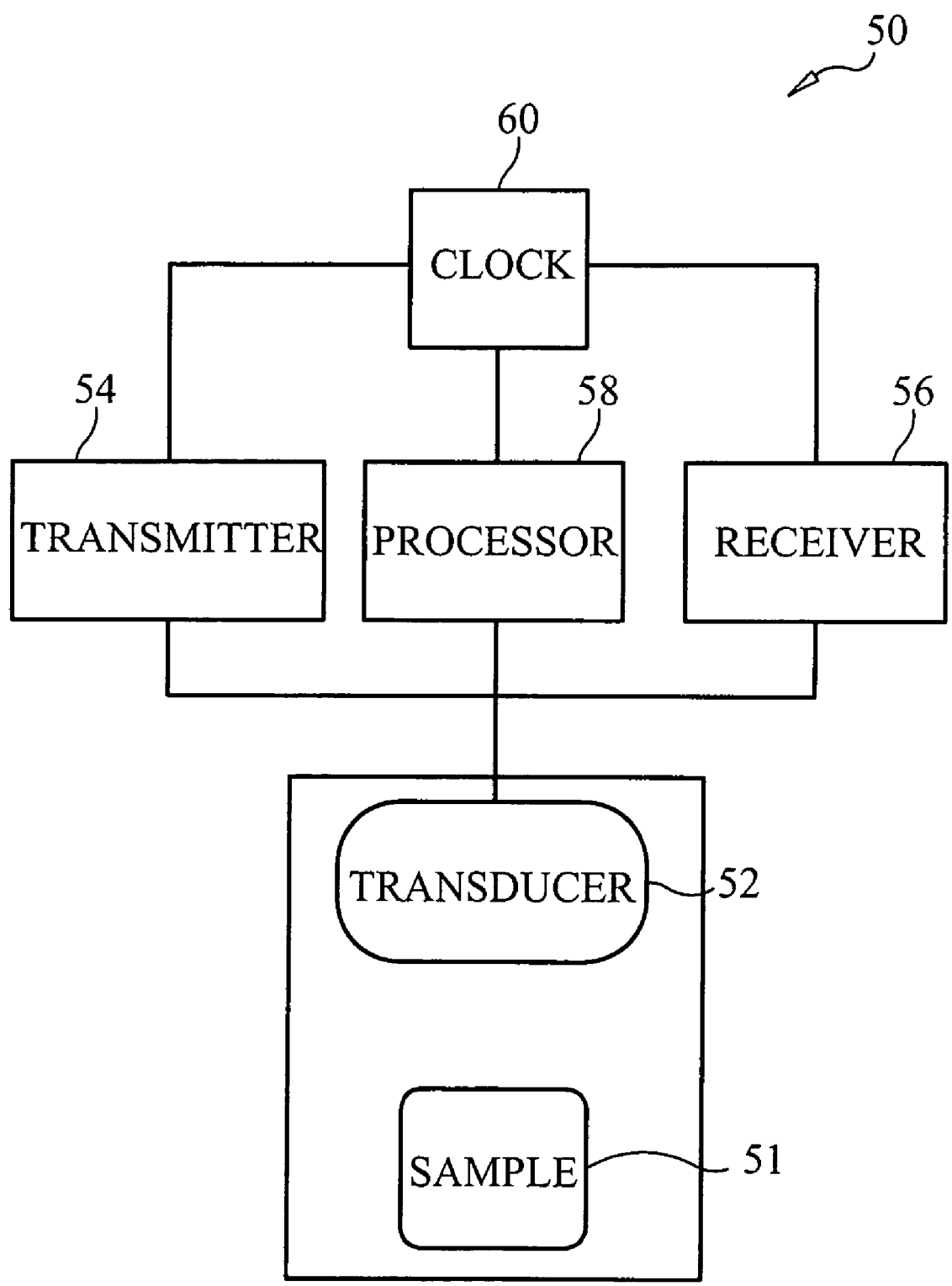
FIG. 2 is a schematic representation of a system for characterization of at lest one physical property of soft tissue.

FIG. 2 shows a schematic representation of an example of a system 50 for characterization of changes in physical properties of soft tissue over time. In this example, a transducer 52, such as may be contained in a device 10 as described above, or directly mounted, fixed to or integral with a container holding a sample 51, for example, is connected to a transmitter 54 as well as receiver 56, both of which are controlled by processor 58 and timed by clock 60.

Clock 60 is provided to control the timing of application of radiation to the sample as generated by transmitter and converted to the acoustic energy at transducer 52, as well as the timing of receiving and interpreting the reflected waves (echoes), by conversion through transducer 52 and receipt of the converted signals at receiver 56, all of which is controlled by one or more processors/microprocessors 58.

Displacements of the soft tissue may be induced by delivering one or more acoustic pulses according to a predetermined frequency through device 10. The displacements may be estimated by applying one or more signal processing algorithms (e.g., minimum sum squared difference motion tracking algorithm, etc.) to the acquired echoes of every nth delivered pulse where "n" is a predefined integer. Alternatively, the signal processing algorithms may be applied to every pulse received. Similarly, algorithms may be applied at every $n^{th}$ time interval for optical waves received. Parameter measurement may be initiated at a predetermined time after one or more coagulation reagents are added to the sample, and such measurements may be repeatedly performed, e.g., once after each passage of a pre-designated time period or according to pre-defined time intervals for measurement. At each acquired time lapse, a time-displacement curve may be generated from which the viscoelastic parameters of the sample can be determined.

Figure 3:
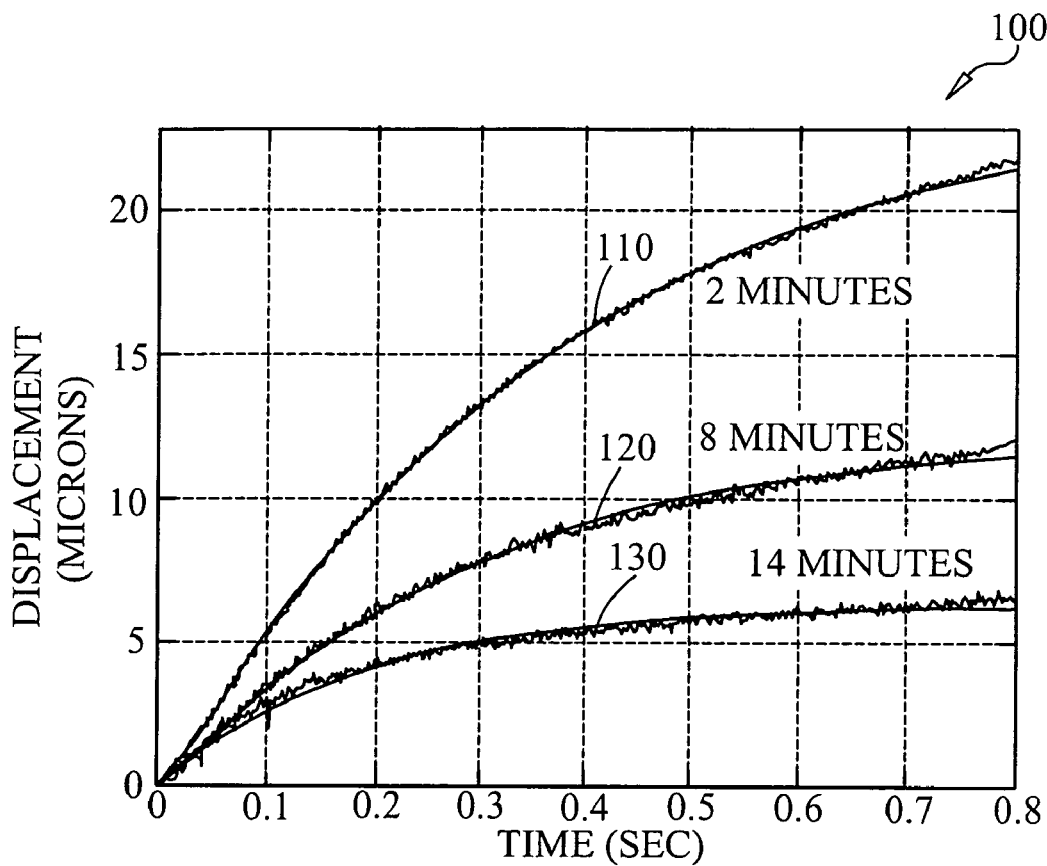
FIG. 3 shows a series of time-displacement curves comparing values predicted by a model to values obtained using an embodiment of the present apparatus.
Figure 4:
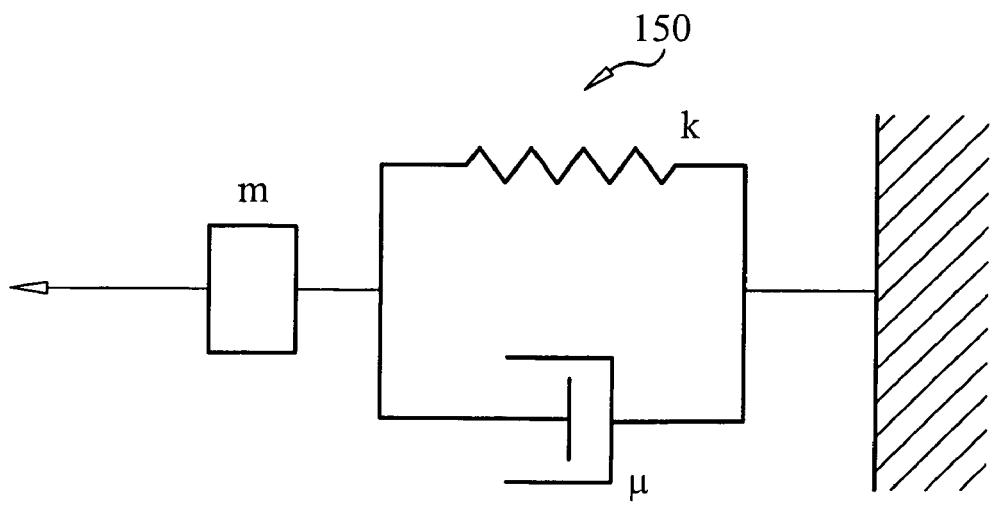
FIG. 4 is a symbolic representation of a modified Voigt model used as a model to characterize the behavior plotted in FIG. 3.

FIG. 3 is a graph 100 showing a set of time-displacement curves 110, 120, 130 obtained during coagulation of a blood sample using the techniques described. Curves 110, 120 and 130 are superimposed on accompanying model predictions, where the mechanical properties of the forming thrombus are modeled by a modified Voigt model 150 as shown in FIG. 4. Experimental results and theoretical predictions show excellent agreement. The basis of the model from which the mechanical parameters are derived is the Voigt model in series with an inertial component.

The modified version 150 of the Voigt model may be used to model the viscoelastic response of blood to acoustic radiation force from which mechanical parameters of the blood may be estimated. Model 150 includes an inertial component "m" in series with the traditional Voigt model, which includes a spring k in parallel with a dashpot μ, as shown in FIG. 4. The governing differential equation for the model is:

$$F(t) = kx(t) + \mu \frac{d}{dt}x(t) + m\frac{d^2}{dt^2}x(t) \quad (4)$$

where F(t) is the applied force as a function of time, x(t) is the induced displacement as a function of time, k is the elastic constant, μ is the viscous constant, and m is the inertial component. System 50 applies radiation force by transmitting a series of pulses to the same location in the blood sample. Assuming that the pulse-to-pulse interval is much shorter than the time constant of the blood's mechanical response, the forcing function may be modeled as a temporal step function as follows:

$$F(t) = Au(t) \quad (5)$$

where A is the force amplitude. Substituting equation (5) into equation (4) and solving for the displacement yields:

$$x(t) = \frac{\zeta = \sqrt{\zeta^2-1}}{2\sqrt{\zeta^2-1}} s \cdot e^{(-\zeta + \sqrt{\zeta^2-1})\omega t} + \frac{\zeta - \sqrt{\zeta^2-1}}{2\sqrt{\zeta^2-1}} s \cdot e^{(-\zeta - \sqrt{\zeta^2-1})\omega t} + s \quad (6)$$

where ζ is the damping ratio, ω is the natural frequency (in radians per second) and s is the static sensitivity. These parameters are defined as:

$$\zeta = \frac{\mu}{2\sqrt{k \cdot m}} \quad (7)$$

$$\omega = \sqrt{\frac{k}{m}} \quad (8)$$

$$s = \frac{A}{k} \quad (9)$$

In the examples described herein, the force scaling constant A was not measured. Thus the time-displacement data in this situation can only be used to solve for relative parameters. To address this limitation, the equations (7), (8) and (9) are redefined according to the following equations (10), (11) and (12) using relative measures of elasticity $k_r$, viscosity $\mu_r$, and mass $m_r$:

$$\zeta = \frac{\mu_r}{2\sqrt{k_r \cdot m_r}} \quad (10)$$

$$\omega = \sqrt{\frac{k_r}{m_r}} \quad (11)$$

$$s = \frac{1}{k_r} \quad (12)$$

where $k_r = k/A$, $\mu_r = \mu/A$ and $m_r = m/A$.

Although the viscosity, elasticity and inertia are measured as force-dependent parameters, the natural frequency and the damping ratio still remain force-free or force-independent parameters. It is further possible to define a third force-independent parameter, i.e., the time constant τ as:

$$\tau = \frac{\mu_r}{k_r} \quad (13)$$

The fact that the actual data shown in FIG. 3 waivers or oscillates somewhat about the model data curves suggest that a different model might be used to even more closely model the behavior. In one possible modification, a dashpot would be placed in series with the model shown in FIG. 4. However, the model of FIG. 4 accurately described the response of the blood during formation of a clot with correlation between the data and the model of FIG. 3 being greater that 99% in most of the cases analyzed.

Example

The following example is put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Figure 5:
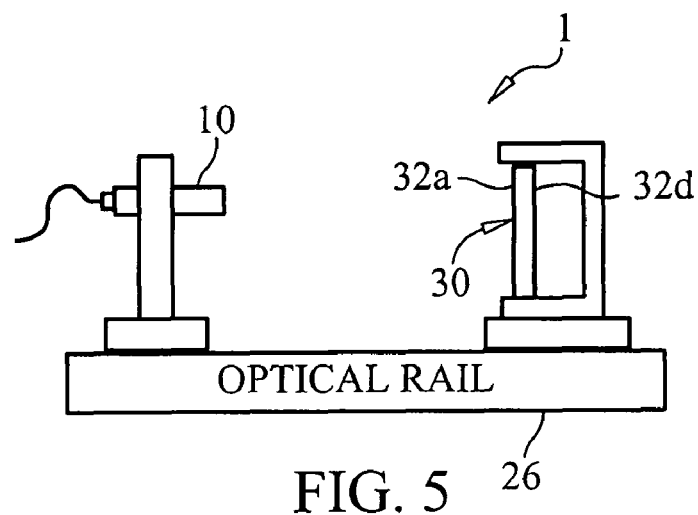
FIG. 5 is a diagrammatic representation of apparatus for in vitro characterization of at least one physical property of soft tissue.

An experimental system 1 as schematically represented in FIG. 5 was used. Device 10 was mounted at one end of a rail and a container 30 was mounted on the opposite end portion of rail 20. Device 10 included a 1.0 cm diameter single piston transducer (General Electric Panametrics V327, Waltham, Mass.) mounted on a five-axis gimbal mount (Newport Corporation, Irvine, Calif.). The transducer had a fixed focus at 4 cm. The transducer was held with the focus at the center of a modified 4.5 mL polystyrene cuvette 30 (Fisher Scientific) that held the blood sample. Cuvette 30 was secured to the rail 20 at a slight tilt so that reflections from the cuvette surface would be directed away from the transducer. Each cuvette 30 was modified by drilling a hole 32a,32d approximately 7 mm in diameter through the front and back sides of cuvette 30 and using silicone sealant (Dow Corning, Baltimore, Md.) to mount a KAPTON® (Dupont, Wilmington, Del.) window over each opening. The KAPTON® windows are acoustically transparent and were provided along the acoustic beam axis of the assembly. The assembly 1 was placed in a water bath held at a room temperature of 21° C.

Transmitted pulses were Gaussian enveloped sinusoids with a center frequency of 10 MHz and a full-width half maximum fractional bandwidth of 75%. The sinusoidal pulses were amplified by 50 dB prior to transmission for a peak-to-peak amplitude of 136 volts. Based on hydrophone measurements performed in the lab, this transmit voltage corresponded to an acoustic intensity ($I_{spta}$) of 300 mW/cm$^2$. A series of 4,000 acoustic pulses were transmitted by the transducer at a pulse repetition frequency of 5 kHz to generate acoustic radiation force within the blood. The returning echoes of every tenth transmitted pulse were acquired in order to estimate displacements induced by radiation force. The same digital clock was used to drive pulse generation and data acquisition, reducing sampling jitter to the order of picoseconds.

To confirm the accuracy of these techniques, preliminary experiments were first performed with a control solution. Results obtained from these preliminary experiments were compared to results obtained from use of a conventional rheometer (TA Instruments AR-2000 constant stress rheometer, available from TA Instruments, Wilmington, Del.). An aluminum double-concentric cylindrical geometry was chose for the conventional rheometer because it is best suited for lower viscosity samples that are not sufficiently solid to maintain their structures under a cone and plate or parallel plate setup.

The control solution consisted of a liquid soap (Clean & Clear® Daily Pore Cleanser, Johnson & Johnson) diluted with deionized water. Although a broad variety of solutions were analyzed, including blood mimicking fluids (for flow measurements) and glycerol solutions, the liquid soap solution specified above was bound to offer an appropriate viscoelastic response while remaining homogeneous and stable over time. Further, the spherical "micro-scrubbers" in the soap were excellent ultrasonic scatterers. The control solution consisted of 60% liquid soap diluted with 40% deionized water. A volume of 20 mL of the control solution was prepared, subsequently vortexed, and placed overnight in a vacuum chamber at 20 mmHg to remove air bubbles trapped within the solution.

Approximately 4 mL of the control solution was placed in a 4.5 mL polystyrene cuvette 30 (having been modified as described above) and secured to rail 20 as described above. A sequence of 4,000 pulses was transmitted according to the experimental protocol previously described. A sequence of ten acquisitions was obtained. The solution was gently stirred with a needle between each acquisition to generate a new speckle pattern and avoid settling of the "micro-scrubbers". The remaining 16 mL of solution was used to perform a creep test in the conventional cylindrical rheometer. Displacement data was obtained from an applied shear stress. Because the amount of force applied by acoustic radiation cannot easily be quantified, the maximum displacement observed according to the present techniques (sonorheometry) in the control solution was used to establish the applied shear stress for the creep test on the conventional rheometer. The computer controlling the conventional rheometer was programmed to perform a sequence of ten repeated creep tests for each acquisition obtained with sonorheometry. The temperature control of the conventional rheometer was set to 21° C. to match the temperature of the water bath during sonorheometry experiments.

Following the completion of the control experiments, sonorheometry experiments were performed on blood samples of approximately 4 mL in volume each. Blood was drawn from four healthy volunteers in their mid-twenties and each sample was placed into a modified 4.5 mL polystyrene cuvette 30 having been modified as described above. One of the four test subjects (referred to as "male 2") indicated a recent history of a clotting disorder (deep vein thrombosis). Thrombin (0.5 units per mL of blood) was immediately added to each drawn blood sample in order to induce coagulation. Each combined sample was inverted multiple times to mix the thrombin within the sample. Each cuvette 30 of coagulating blood was mounted to the rail 20 as described above. Sonorheometry experimental protocol was initiated within two minutes of the addition of thrombin. Sonorheometry measurements were repeated over a seventy minute period in order to characterize the blood sample for each respective cuvette 30. Data was acquired every minute for the first ten minutes, every two minutes for the next ten minutes, every three minutes for the next fifteen minutes, and finally, every five minutes for the next thirty-five minutes for a total of twenty-six acquisitions per sample.

The sum squared differences (SSD) algorithm was applied between the first and the $n^{th}$ echoes (where n is a Predefined integer that defines how often echoes or waves are considered to estimate a tissue displacement measurement; in this example, n was set to 10) to determine the tissue displacement at a given range, see Viola et al., "A Comparison of the Performance of Time Delay Estimators in Medical Ultrasound", IEEE Transactions on Ultrasonics, Ferroelectrics, and Frequency Control, vol. 50, no. 4, pp. 392-401, 2003.

Specifically, Viola et al. describes: Time Delay Estimation (TDE) is a common operation in ultrasound signal processing. In applications such as blood flow estimation, elastography, phase aberration correction, and many more, the quality of final results is heavily dependent upon the performance of the time-delay estimator implemented.

In the past years, several algorithms have been developed and applied in medical ultrasound, sonar, radar, and other fields. In this paper we analyze the performances of the widely used normalized and non-normalized correlations, along with normalized covariance, sum absolute differences (SAD), sum squared differences (SSD), hybrid-sign correlation, polarity-coincidence correlation, and the Meyr-Spies method. These techniques have been applied to simulatrasound radio frequency (RF) data under a variety of conditions. We show how parameters, which include center frequency, fractional bandwidth, kernel window size, signal decorrelation, and signal-to-noise ratio (SNR) affect the quality of the delay estimate. Simulation results also are compared with a theoretical performance limit set by the Cramer-Rao lower bound (CRLB).

Results show that, for high SNR, high signal correlation, and large kernel size, all of the algorithms closely match the theoretical bound, with relative performances that vary by as much as 20%. As conditions degrade, the performances of various algorithms differ more significantly. For signals with a correlation level of 0.98, SNR of 30 dB, center frequency of 5 MHz with a fractional bandwidth of 0.5, and kernel size of 2 µs, the standard deviation of the jitter error is on the order of a few nanoseconds. Normalized correlation, normalized covariance, and SSD have an approximately equal jitter error of 2.23 ns (the value predicted by the CRLB is 2.073 ns), whereas the polarity-coincidence correlation performs less well with a jitter error of 2.74 ns.

I. INTRODUCTION

Estimation of the time delay between signals is critical to may applications within medical ultrasound. Precise and robust time-delay estimation allows for accurate blood velocity estimation, phase aberration correction, and elastography imaging. Because of its importance, time-delay estimation has long been an active research topic with numerous techniques developed. These methods include, but are not limited to, normalized and non-normalized cross correlation, normalized covariance, sum absolute differences (SAD), sum squared differences (SSD), polarity-coincidence correlation, hybrid-sign correlation, and the Meyr-Spies method. Along with the development of those techniques, several lower bounds have been derived that can analytically predict a lower limit on the performance of a time-delay estimator. These bounds include the Cramer-Rao (CRLB), the Barankin, and the Ziv-Zakai lower bounds.

Although they exhibit high computational cost (in terms of point operations), normalized cross correlation and normalized covariance often are said to yield optimal estimates. The main advantage of these two algorithms is that they consider the energy of the two signals and are thus able to generate more precise estimates. The normalized covariance differs from the normalized correlation because it takes into account the means of the reference and delayed signals over the observation windows. The SAD and SSD algorithms have been show to perform as precisely as the normalized cross correlation, at least in two-dimensional (2-D), and have a reduced computational complexity. This reduced complexity arises from two main factors, the elimination of multiplications and particularly the elimination of the normalization. Polarity-coincidence, also called one-bit correlation, and hybrid-sign correlation are binary and half-binary correlation algorithms, respectively. These two techniques have been developed in order to reduce computational and hardware costs. The one-bit correlation has been shown to give a lower variance estimate of blood velocity when compared with the conventional baseband auto-correlation. Non-normalized correlation also has been used extensively for delay estimation, yielding reasonable results in term of precision and speed of execution. The main difference between normalized and non-normalized correlation is that the energy of the signals is not taken into account in the latter algorithm, thus reducing the number of point operations. The Meyr-Spies method is described in the literature as a technique for noncontact velocity measurements. It is analogous to the non-normalized correlation; it works by properly combining reference and delayed signals.

For all of these algorithms, the quality of the estimates may be corrupted by a variety of factors. First, the estimation process is typically performed using signals which have been sampled in time. This means that the sampling rate quantizes the possible delay estimates, and thus introduces potential errors. Interpolation can be used to mitigate errors due to sampling.

The reference and delayed signals also are degraded by electronic nose and decorrelated by physical processes. These factors, along with the use of finite length signals, introduce two types of errors commonly called false peak and jitter errors. False peak errors arise when there exists a second correlation peak with a higher (lower in the case of SAD or SSD) amplitude than the peak corresponding to the real displacement Ambiguity (or false peak) errors result form the sue of a finite bandwidth. It has been show that, in the presence of false peak errors, the actual performance of a time-delay estimator may be worse than that predicted by the CRLB. In such cases, the Barankin or the Ziv-Zakai bounds should be used instead of the CRLB.

Although the inclusion of false peak errors may significantly degrade TDE performance, their impact is by no means certain. In many applications the physics of the problem induces continuity conditions that make nonlinear detection and removal of false peaks possible. For example, phase aberrators are the result of tissue structure and therefore are unlikely to change greatly between adjacent array elements. Thus, false peak errors in phase aberration measurement or correction should appear as discontinuities in the phase aberration profile, making them easy to detect and remove. For flow estimates, nonlinear processing techniques such as temporal and spatial median filtering may be used to remove false peaks. Lubkinski et al., "Speckle tracking methods for ultrasonic elasticity imaging using a short-time correlation," IEEE Trans. Ultrason., Ferroelect., Freq. Const., vol. 46, no. 1, pp. 82-96, 1999 have shown that, in strain imaging, false peak errors can be overcome by spatially filtering the correlation coefficient function prior to displacement estimation. The same group also showed that signal correlation can be improved and false peak errors reduced by using a number of small compression steps instead of one large compression step. Furthermore, in elastography imaging signals generally possess high SNR, and thus the performances of the time-delay estimator approaches the limit imposed by the CRLB when a short search window is used.

However, jitter errors appear as a small displacement in the peak of the correlation curve. They cannot be removed, and thus they place a fundamental limit on the accuracy of the estimation process. Walker and Trahey, "A fundamental limit on delay estimation using partially correlated speckle signals," IEEE Trans. Ultrason., Ferroelect., Freq. Contr., vol. 42, no. 2, pp. 301-308, 1995 adapted the CRLB to predict the magnitude of jitter errors for ultrasound radio frequency (RF) data.

In this paper, we analyze the performances of numerous unbiased time-delay estimators in terms of their jitter errors. We have simulated a broad variety of conditions and compared the results to the theoretical limit given by the CRLB. We present simulation results depicting the magnitude of the jitter errors of the various algorithms as a function of SNR, window length, center frequency, fractional bandwidth, and correlation coefficient. By comparing the algorithms under identical conditions, it is possible to determine quantitative tradeoffs between performance and computational complexity.

II. THEORY

Delay estimation is performed on a pair of signals that we represent mathematically as:

$$r_1(t) = s_1(t) + n_1(t),$$

$$r_2(t) = s_2(t) + n_2(t), \quad (1v)$$

where, $r_1(t)$ and $r_2(t)$ are two random processes that represent the reference and the delayed signals. In this expression, $s_1(t)$ and $s_2(t)$ are the echo signals received by the transducer. These signals may have been decorrelated by physical processes. Also note that there exists a time delay between $s_1(t)$ and $s_2(t)$, which we assume to be zero in this paper, without a loss of generality for unbiased estimators. The $n_1(t)$ and $n_2(t)$ represent additive noise that is introduce from electronic sources. It is assumed that the nose terms are uncorrelated to one another and to the signals. Furthermore, we assume that both the signals and noise are zero-mean, stationary, Gaussian random processes. The stationary property of the processes is valid only when considering short-time windows, as the signal amplitude tends to decay exponentially with range due to frequency-dependent attenuation. In many ultrasound applications, we may assume that $s_1(t)$ and $s_2(t)$ have power spectra with possibly different spectral heights, but with the same shape.

Because only finite windows of data are available, the ideal correlation curve cannot be estimated, and thus alternative methods must be used for time-delay estimation. In this paper we consider the following TDE algorithms:

1. Normalized Correlation:

$$R_{nc}(\tau) = \frac{\int_{-T/2}^{T/2} (s_r(t) s_d(t+\tau)) dt}{\sqrt{\int_{-T/2}^{T/2} (s_r(t))^2 \, dt \int_{-T/2}^{T/2} (s_d(t+\tau))^2 \, dt}} \quad (2v)$$

2. Sum Absolute Differences (SAD):

$$R_{SAD}(\tau) = \int_{-T/2}^{T/2} |s_r(t) - s_d(t+\tau)| \, dt \quad (3v)$$

3. Normalized Covariance:

$$R_{NCov}(\tau) = \frac{\int_{-T/2}^{T/2} (s_r(t) - \overline{s_r})(s_d(t+\tau) - \overline{s_d}(\tau)) dt}{\sqrt{\int_{-T/2}^{T/2} (s_r(t) - \overline{s_r})^2 \, dt \int_{-T/2}^{T/2} (s_d(t+\tau) - \overline{s_d}(\tau))^2 \, dt}} \quad (4v)$$

where, $$\overline{s_r} = \left(\frac{1}{T}\right) \int_{-T/2}^{T/2} s_r(t) \, dt$$

-continued $$\overline{s_d}(\tau) = \left(\frac{1}{T}\right)\int_{-T/2}^{T/2} s_d(t+\tau)\,dt$$

4. Non-Normalized Correlation:

$$R_{NNC}(\tau) = \int_{-T/2}^{T/2} s_r(t)s_d(t+\tau)\,dt \tag{5v}$$

5. Sum Squared Differences (SSD):

$$R_{SSD}(\tau) = \int_{-T/2}^{T/2} (s_r(t) - s_d(t+\tau))^2\,dt \tag{6v}$$

6. Hybrid-Sign Correlation:

$$R_{HSC}(\tau) = \int_{-T/2}^{T/2} s_r(t)\text{sign}(s_d(t+\tau))\,dt \tag{7v}$$

where, $$\text{sign}(x) = \begin{cases} 1 & \text{if } x > 0 \\ -1 & \text{if } x < 0 \\ 0 & \text{if } x = 0 \end{cases}$$

7. Polarity-Coincidence Correlation (One-bit Correlation):

$$R_{PCC}(\tau) = \int_{-T/2}^{T/2} \text{sign}(s_r(t))\text{sign}(s_d(t+\tau))\,dt \tag{8v}$$

8. Meyr-Spies Method:

$$R_{MSM}(\tau) = \int_{-T/2}^{T/2} (-s_r(t) + s_r(t-2))(s_d((t-1)+\tau))\,dt \tag{9v}$$

In these mathematical expressions, T represents the kernel window length, whereas $\overline{s_r}$ and $\overline{s_d}(\tau)$ are the means of the reference and delayed signals over such a window.

Each of these algorithms is subjected to jitter errors which cannot typically be eliminated and thus unrecoverably degrade time delay estimates. The minimum degree of this degradation can be predicted theoretically using the Cramer-Rao Lower Bound (CRLB). The CRLB predicts the standard deviation of jitter errors when the reference and delayed signals are relatively similar. It places a theoretical limit on the performance of all unbiased time delay estimators. The CRLB was derived by Walker and Trahey for ultrasonic speckle signals following the work done by Carter in the radar and sonar literature.

According to their derivation, the standard deviation of the jitter errors for any unbiased estimator is given by:

$$\sigma(\Delta t - \hat{\Delta t}) \geq \sqrt{\frac{3}{2f_o^3 \pi^2 T(B^3 + 12B)}\left(\frac{1}{\rho^2}\left(1 + \frac{1}{SNR^2}\right)^2 - 1\right)} \tag{10v}$$

where, $\Delta t$ and $\hat{\Delta t}$ are the true and estimated displacement, respectively. Equation (10) shows how parameters such as center frequency $f_o$, fractional bandwidth B, signal decorrelation $\rho$, electronic signal-to-noise ratio SNR, and kernel window length T, affect the standard deviation of the jitter, and thus determine the quality of the estimate. Also note that if equation (10) is normalized by the temporal period, and the jitter expressed as an error relative to the signal period, rather than an absolute error, then the dependence upon frequency changes from $f^{-3/2}$ to $f^{-1/2}$.

III. SIMULATIONS

Simulations were performed to test the performance of the various time delay estimators and to compare those results to the theoretical bound given by Eq. (10v). The standard deviation of the jitter was found for each estimator as parameters including electronic SNR, correlation coefficient, center frequency, fractional bandwidth, and kernel window length were varied. For each condition analyzed, a set of 1,000 reference and delayed signals were generated, and the estimators given by equations (2v)-(9v) were applied. The peak of the correlation curves were located within an interval of one half period in length centered about the true displacement. Reference and delayed signals were generated by combining appropriate base signals, according to:

$$s_r(t) = s_{b1}(t) + \frac{1}{SNR}s_{b3}(t) \tag{11v}$$

$$s_d(t) = W_{1,2}s_{b1}(t) + W_{2,2}s_{b2}(t) + \frac{1}{SNR}s_{b4}(t)$$

where, $s_{b1}(t)$, $s_{b2}(t)$, $s_{b3}(1)$, $s_{b4}(t)$ are base signals, and $W_{i,j}$ is an element of the matrix determined by the Cholesky factorization of the cross correlation matrix. The matrix W is given by:

$$W \cdot W^t = \begin{bmatrix} 1 & \rho \\ \rho & 1 \end{bmatrix} \tag{12v}$$

In this expression $W^t$ represents the transpose of the matrix W and $\rho$ is the desired correlation coefficient. The signals $s_r(t)$ and $s_d(t)$ were interpolated to a sampling rate of 200 times the center frequency, so as to reduce the effects of sampling errors. Base signals were created by convolving Gaussian noise (zero-mean, and unit standard deviation) with a sinc-enveloped sinusoid given by:

$$psf(t) = \frac{\sin(\pi B f_o t)}{\pi B f_o t}\sin(2\pi f_o t) \tag{13v}$$

where, B is the fractional bandwidth, and $f_o$ is the center frequency. Although there are several point spread function models that can be used to mimic real ultrasonic data, in this paper we have used the sine-enveloped sinusoid because it results on a flat band limited spectra, which is consistent with the signal spectra assumed to derive the CRLB in equation (10v).

The standard deviation of the jitter was then calculated using:

$$\hat{\sigma}(\Delta t - \hat{\Delta t}) \sqrt{\frac{1}{1000} \sum_{j=1}^{1000} (\Delta t - \hat{\Delta t}_j)^2} \quad (14v)$$

where, $\Delta t$ and $\hat{\Delta t}$ are the true and estimated time delays, as defined for equation (10v). Since we assume that $\Delta t=0$, equation (14v) does not discriminate between errors due to a bias (accuracy) and error due to standard deviation (precision). However, prior to apply equation (14v) we examined the histogram of every set of conditions and found that the estimators were unbiased under all conditions analyzed (i.e., the mean delay estimate was equal to zero). This validates the use of equation (14v) as a measure of the precision of the estimators.

IV. RESULTS

Simulations were performed by applying the various time delay estimation algorithms to synthetic ultrasonic RF data. All calculations were performed in MatLab (MathWorks Inc., Natick, Mass.). The default simulation conditions assumed a 5 MHz center frequency, 50% fractional bandwidth, correlation coefficient of 0.98, electronic SNR of 30 dB, and kernel window length of 2 microseconds.

For all parameters other than SNR, the default values were used. As would be expected, jitter is lower at high SNRs. As to the standard deviation of jitter as a function of the kernel length, jitter magnitude, as estimated by simulations, falls as the window length increases.

We also determined 95% confidence intervals for the standard deviation of the jitter errors for a subset of the conditions analyzed in this paper. In order to obtain statistically significant results, the confidence intervals were based on a set of 4,000 reference and delayed signals. The upper and lower limits of the intervals were computed by multiplying the estimated value of the standard deviation by $$\frac{1}{1 \pm 1.96/\sqrt{2\cdot(N-1)}},$$

where N is the number of iterations (in this case N=4,000). The confidence intervals for the various algorithms were calculated using the default values for all the parameters.

V. DISCUSSION

The results presented in this paper show that optimal TDE performance is obtained for high values of SNR, correlation coefficient, kernel window length, center frequency, and fractional bandwidth. These results are intuitive and in agreement with equation (10v), and with previously presented results.

For SNR values between 15 dB and 30 dB, the performance of all the estimators closely matches the CRLB. It can be further noted that jitter magnitude for all the techniques tested increases dramatically as the SNR falls below 10 dB. Surprisingly, as the SNR falls from 0 dB to −5 dB, the standard deviation of jitter errors for the eight algorithms move closer to the value predicted by the CRLB. Since the CRLB is expected to be accurate under "good" conditions, one would expect jitter to continue to grow above the bound as conditions worsen. The displacement histograms for this condition showed accumulation at the limits of the search region for all the estimation algorithms, indicating that the search region was too small to contain the errors under these conditions. This phenomenon was also observed by Walker and Trahey. In order to obtain a more realistic measure of the performances of the estimators for this value of the SNR, we performed additional simulations with increased search window size, and found that the jitter magnitude continued to increase well above the value predicted by the CRLB. The estimated standard deviations were on the order of 87 nanoseconds for all the estimators.

Above 20 dB there are differences of up to 20% between the best and the worst estimators. This 20% difference represents a significant variation in the performance of these estimators. We also found that the SSD, normalized correlation, and normalized covariance track displacements with more precision than the other algorithms tested.

For large kernel lengths, it was observed that the eight techniques exhibit similar performance, with all coming close to the CRLB. When conditions degrade and smaller windows are used, the standard deviation of jitter errors increases somewhat, and the various algorithms show more significant differences in performance.

For each of the algorithms examined, the use of a larger window resulted in a smaller jitter error. This is not surprising since a larger window contains more information about the signals. For a kernel window of 8 microseconds, the jitter magnitude for all the estimators is roughly 1 nanosecond. For the stationary signal model used here, the use of a large window helps to reduce jitter errors. However, in applications such as blood flow estimation or strain estimation the use of a large window will cause a loss in spatial resolution and result in significant signal decorrelation. Furthermore, large windows may be undesirable because of the high computational costs associated with their processing.

Differences of 15% to 30% were observed in the relative performance of the various estimators. SSD, normalized correlation, and normalized covariance exhibited a lower standard deviation of jitter errors than the other algorithms tested.

Regarding jitter magnitude as a function of correlation coefficient, for correlations above 0.9, there is a close match between theoretical bound and simulation results for all the algorithms tested. As the correlation between reference and delayed signals falls to 0.5, the jitter magnitude increases by almost a factor of 10 with respect to the case of perfect correlation, and the performance of all the algorithms becomes significantly worse than that predicted by the CRLB. This is to be expected since the CRLB assumes that reference and delayed signals are very similar.

At a correlation level of 0.5, most of the estimators are grouped together with nearly identical performance. For correlation coefficients greater than 0.9, performances of the algorithms separate with relative differences of about 20% between the best and the worst algorithms. At a correlation coefficient of 1.0, the difference in jitter errors between normalized correlation and polarity-coincidence correlation is roughly 40%. Once again, SSD, normalized correlation, and normalized covariance outperform the other algorithms.

Simulations were run to study the dependence of jitter on center frequency. A fractional bandwidth of 0.5 was used for this series of simulations. When the center frequency is greater than 5 MHz, simulation results closely match the theoretical bound. For frequencies greater than 7 MHz, the standard deviation of jitter errors is on the order of 1 nanosecond.

At a frequency of 1.5 MHz, the performance of the various algorithms covers a fairly broad range, from about 13.6 nanoseconds for the SSD, to about 18 nanoseconds for the polarity-coincidence correlation. When the center frequency was held constant to the default value of 5 MHz, the fractional bandwidth has little impact in differentiating the relative performances of the algorithms tested. Under all the conditions analyzed, the estimators show the same performance distribution. Once again, SSD, normalized correlation, and normalized covariance outperform the other algorithms with a relative difference of about 20%.

The 95% confidence intervals of the estimated jitter standard deviation presented results that are intuitive, and in agreement with other results in this paper. They show that normalized correlation, normalized covariance, and SSD are more precise in a statistically meaningful way than the other algorithms examined.

The simulations presented in this paper show that normalized correlation, normalized covariance, and SSD outperform the other algorithms tested. For most of the conditions analyzed, the performances of these three algorithms, in terms of their jitter errors, are almost identical. Both normalized correlation and normalized covariance take into account the energy of the reference and the delayed signals in their mathematical formulations. Thus, these two algorithms are the only ones with the ability to compensate for local variations in the mean and standard deviation of the signals. They retain more signal information than the other algorithms, and are therefore able to produce more precise estimates. However, these algorithms also incur a high computational cost, a significant drawback for real-time implementation.

The SSD works by summing the square of the difference between the two signals. Except for a scaling factor, its definition is analogous to that of the mean squared error (MSE) between reference and delayed signals. The MSE is a measure of the performance of a point estimator, often used in non-linear regression algorithms. The MSE is a very powerful metric, and this similarity may help to explain why the SSD performs so well.

The SAD sums the absolute value of the difference between reference and delayed signals. Summing the difference between two vectors doesn't emphasize large differences as much as the MSE, and thus SAD doesn't perform as precisely as the SSD does. Friemel et al. have shown that SAD has performance comparable with that of normalized correlation, and that this algorithm doesn't compensate for local variations in the mean and variance of the signals. In this paper we have shown that SAD generally performs with less precision than the normalized correlation and normalized correlation. This contradicts earlier work by Friemel et al., perhaps because their analysis utilized 2D data sets, where more information about the signals is available for processing. Both the SSD and SAD have lower computational costs than the normalized correlation and normalized covariance.

The non-normalized correlation is analogous to the normalized correlation, except that this algorithm does not normalize by the energy of the pair of signals used. Thus, the non-normalized correlation is strongly dependent upon variations in mean and standard deviation of the signals. A local high amplitude region is likely to skew the estimates of this algorithm.

Friemel et al. observed that the non-normalized correlation is highly sensitive to variations in kernel size. A larger observation window contains more independent samples, and thus local variations in the signal mean and variance are reduced, resulting in an improvement in the quality of the time delay estimates. Our results agree with this observation. With a lower computational cost than normalized correlation and normalized covariance, non-normalized correlation is an attractive algorithm when large windows of data are available.

The Meyr-Spies method was developed as a velocity estimation technique for non-contact measurements. This algorithm works by shifting in time and combining together reference and delayed signals. Its definition is similar to that of non-normalized correlation, and thus similar insights regarding performance apply.

For almost all the conditions investigated in this paper, the hybrid-sign and the polarity-coincidence algorithms performed worse than the other algorithms. The polarity-coincidence correlation works by taking the sign function of both the reference and delayed signals, whereas the hybrid-sign correlation takes the sign function of either the reference or the delayed signals. The polarity-coincidence and the hybrid-sign correlations are also known as fully binary and half binary estimators, respectively. The sign function greatly reduces the amount of information available, and thus the precision of these two techniques is significantly reduced. The main advantage of these two techniques is that they are relative easy and cheap to implement in hardware.

We have also examined the execution time associated with the various algorithms in MatLab. We calculated the average execution time for each algorithm, based on a series of 1000 repetitions. The results obtained were somewhat surprising. The normalized correlation was one of the faster algorithms, whereas the polarity-coincidence method was one of the slower. MatLab is highly optimized for floating point matrix operations and this may explain the results observed. The computational costs are thus platform and software dependent. We believe that the implementation of these eight algorithms in other software, such as C, will produce results more intuitive and consistent with the number of point operations employed.

Note that throughout this paper we have used a simple model in which decorrelation acts uniformly across the frequency spectrum of the signals. Although this model works quite well in cases such as motion compensation for synthetic aperture imaging and for signals obtained from adjacent elements in the absence of phase aberration, it might be not ideal for some medical imaging situations. However, performing a general study and simultaneously using a thorough detailed model is impossible given that a different decorrelation model would need to be applied for every specific field of application. In phase aberration correction for example, it has been shown by Walker and Trahey that the rate of decorrelation of received speckle signals is dependent upon frequency. In other applications, such as blood flow measurement, the correlation of received echo signals is a function of a variety of factors which include flow velocity gradient, angle between ultrasonic beam and axial velocity in the vessel, and operating frequency. In elastography, decorrelation between pre and post compression RF signals is dependent upon range, and geometry of the target.

As shown in this paper, the relative differences in performance between the eight algorithms range from 15% to about 40%. Although these differences may seem negligible, in practical applications error accumulations can make them significant. For example, phase aberration correction requires the combination of multiple time delay estimates in order to estimate the aberrator profile. As the time delay estimates are combined, their errors accumulate to a greater overall error. In this and other applications, error accumulation can make the choice of TDE an important one.

VI. CONCLUSIONS

The performance of eight commonly used time delay estimators have been compared through computer simulation. The standard deviation of jitter errors under the conditions of varying SNR, kernel length, correlation coefficient, center frequency, and fractional bandwidth was used as the metric for comparison. The results presented show that normalized correlation, normalized covariance, and SSD perform 15% to 40% better than the other algorithms under all conditions analyzed. The polarity-coincidence and the hybrid-sign correlations perform the worst. The SAD, non-normalized correlation, and the Meyr-Spies method showed intermediate performance.

These results suggest that the SSD algorithm represents an excellent choice in terms of both performance and computational efficiency.

In the present application, sub sample delays were estimated by identifying the location of the peak of a parabolic fit about the minimum of the SSD grid. The ensemble of these displacement estimates form a time-displacement curve that holds combined information about both elastic and viscous components of the blood sample being analyzed.

In order to model the viscoelastic response of coagulating blood to thus estimate the mechanical parameters, the modified version of the Vogt model (described above with regard to FIG. 4) was applied to the experimental data acquired. The governing differential equation for this application is equation (1) above. Device 10 of system 1 applied radiation force by transmitting a series of 4,000 ultrasonic pulses to the same location within the blood sample.

Figure 6A:
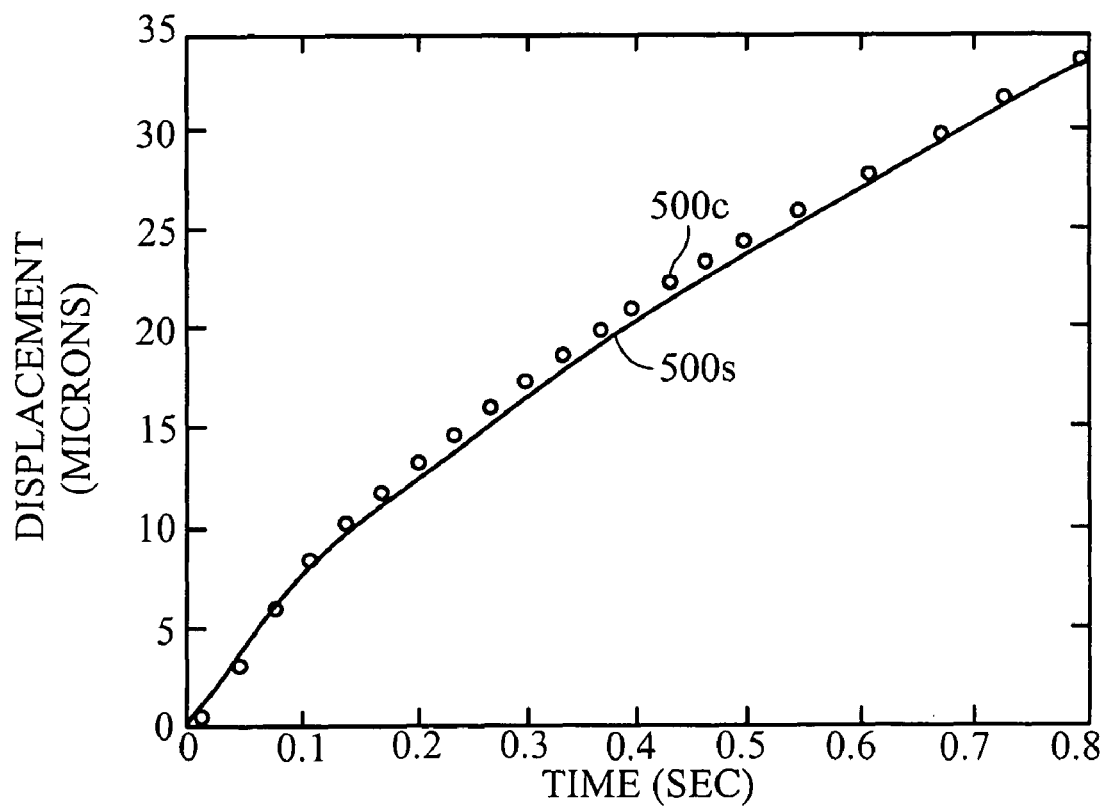
FIGS. 6A, 6B and 6C show a portion of the results obtained from analyzing a control solution as described in the Example below.
Figure 6B:
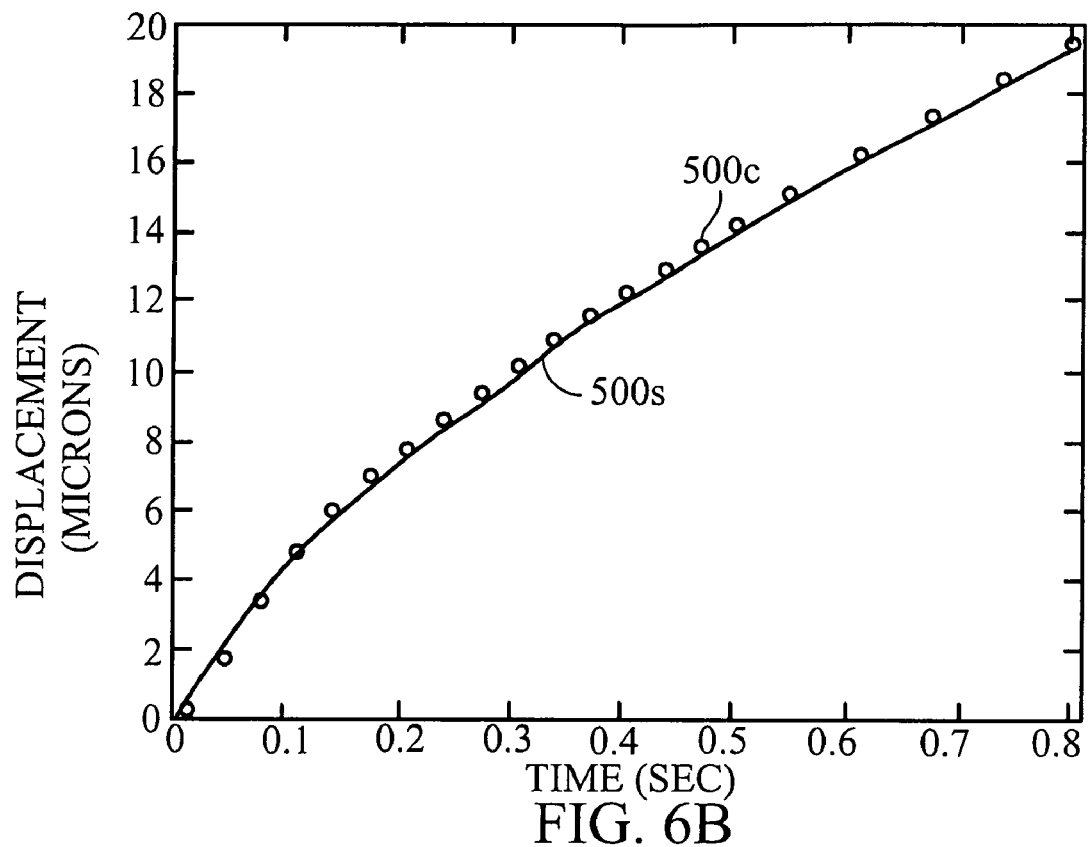
Figure 6C:
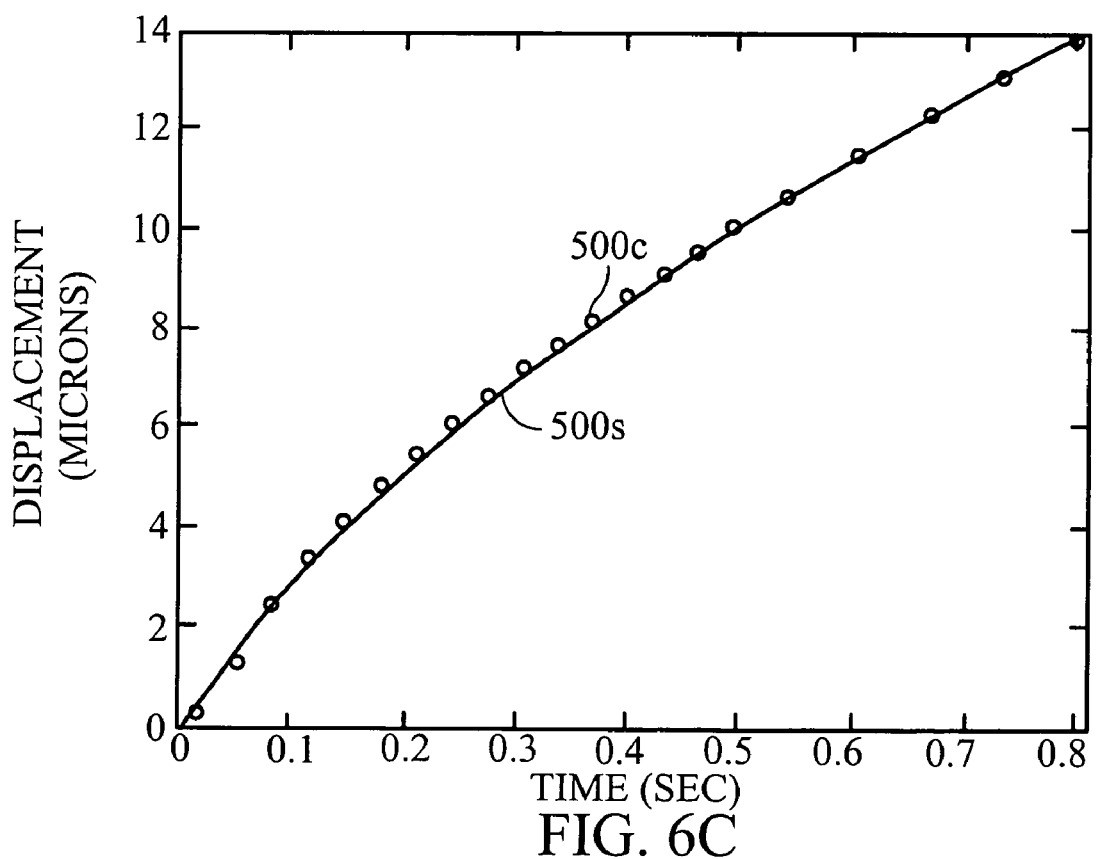

A portion of the results obtained from analyzing the control solution is shown in FIGS. 6A-6C. Of one hundred paired time-displacement curves, each overlaying a curve obtained via sonorheometry over a corresponding curve obtained with the convention cylindrical rheometer, three such curves are shown, see FIGS. 6A-6C, respectively. The sonorheometry data is presented as a continuous line 500s, while the conventional cylindrical rheometer data is displayed by circles 500c. Similar results to those shown were obtained for the remainder of the control experiments. The correlation coefficient between the data obtained by the two methods ranged from 0.9990 to 0.9999, with an overall mean correlation coefficient of 0.9993.

Figure 7:
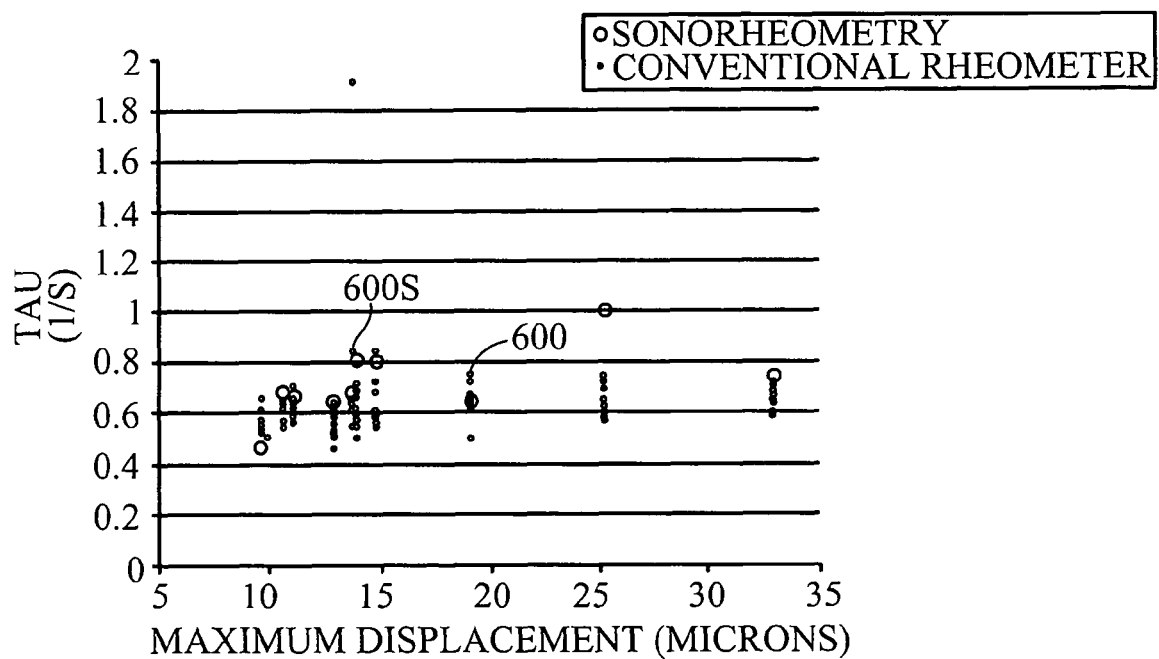
FIG. 7 shows comparative time constants for convention rheometry uses as compared to use of the present techniques.

FIG. 7 shows estimated time constants (i.e., "tau" or "τ") as a function of maximum achieved displacement. Black circles 600s represent the time constants estimated from the present methods (sonorheometry) while gray diamonds 600c represent the estimates from the conventional rheometer. The time constants, as shown, have values ranging from approximately 0.45 to 1.91 seconds, while the majority of the time constants lie around 0.6 seconds.

Figure 8:
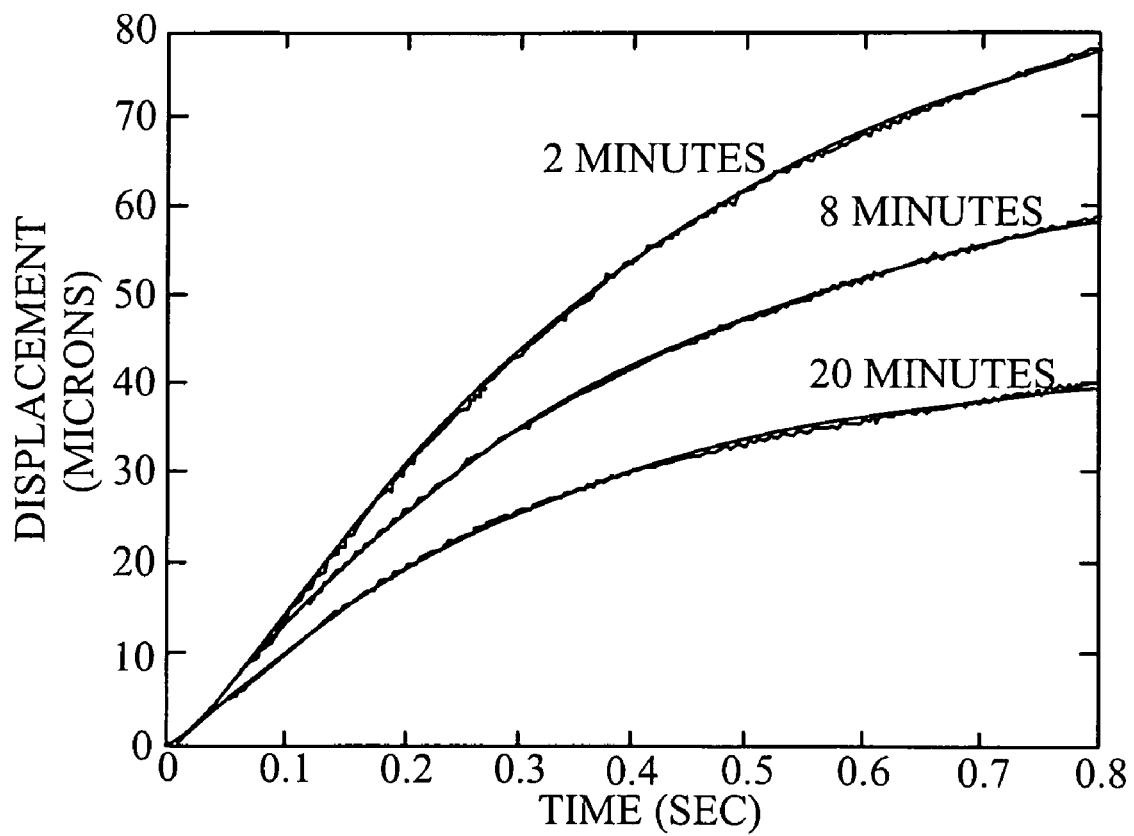
FIG. 8 shows a set of time-displacement curves obtained from one blood sample along with the accompanying best fit model predictions, as described below in the Example.

FIG. 8 shows a set of time-displacement curves obtained from one blood sample along with the accompanying best Fit model predictions. The predictions are the smooth lines and the time displacement curves generated from the experimental data are the slightly wavering lines. The displayed curves indicate displacement at the same axial location with cuvette 30 for a single sample taken from female subject 2. Although coagulation data was acquired at twenty-six time intervals in the seventy minute experimental period, for sake of simplicity, only the experimental curves obtained at two, eight and twenty minutes have been displayed. Similar curves were obtained for the other acquisition times. Experimental results and best fit models show excellent agreement. The peak-to-peak error in displacement estimates was on the order of 0.5 microns.

Maximum detected displacement of the blood samples progressively decreased as a blood clot started to form in each respective cuvette 30. After a certain amount of time, which was unique to each subject, no appreciable displacement could be detected. The results also suggested that the axial position from which displacements were detected became progressively narrower with the passage of time.

The estimated (calculated) relative modulus of elasticity and relative viscosity values clearly showed that the relative modulus of elasticity increased as the clot formed, and this was consistent for all four subjects tested. As to viscosity, the two female subjects showed increasing relative viscosity as the clots were forming, while for the male subjects, relative viscosity remained fairly constant, with some increase near the conclusion of coagulation.

As to force-free (force independent parameters), the time constant, expressed in seconds, decreased with time for all four subjects, which was expected since the blood becomes stiffer as time elapses. For example, the time constant of the "female 1" subject decreased from about 0.6 seconds at the two minute test time to a value of about 0.3 seconds at the twenty minute test time, and the time constant of the "male 2" subject had a value of 0.45 seconds at the two minute test time and decreased to 0.2 seconds at the sixteen minute test time. Similar trends were observed for damping ratios, where clotting blood exhibits lower values. As expected, blood samples are always over-damped systems. In contrast with the other two force-free parameters examined, natural frequency increases as blood is coagulating, reaching values of about 500 rad/sec (for female 1 and female 2).

The invention claimed is:

1. A method of characterizing at least one physical property of a biological material, said method comprising:
   generating a series of acoustic pulses and directing said series of pulses into the material such that at least one of the pulses is of sufficiently high intensity to induce physical displacement of the material, and wherein each of said acoustic pulses is of finite duration and of brief duration relative to a duration of said generating and said directing;
   controlling a temperature of the material;
   measuring a displacement, either directly or indirectly, of the material resulting from said induced physical displacement thereof, wherein the temperature of the material is controlled over a duration of said measuring a displacement; and
   estimating at least one characteristic of the physical displacement based on said measuring.

2. The method of claim 1, wherein said measuring step comprises receiving at least two of said acoustic pulses reflected from the material and wherein said estimating comprises establishing a baseline based on at least one of said acoustic pulses received, and calculating an estimate of said at least one characteristic based on comparison of at least another of said acoustic pulses received to said baseline.

3. The method of claim 1, wherein said measuring step comprises receiving optical reflections from the material as the material is being physically displaced and said estimating is based on the optical reflections received.

4. The method of claim 1, wherein said measuring step comprises receiving at least two of said acoustic pulses reflected from a container or membrane in contact with the material that moves with the material.

5. The method of claim 1, wherein the material comprises soft tissue.

6. The method of claim 1, wherein the material comprises blood.

7. The method of claim 6, wherein said controlling the temperature of the material comprises placing the blood in contact with a second material, said second material having a controlled temperature.

8. The method of claim 7, wherein said controlling comprises controlling the temperature of the blood without placing the blood or material in a bath.

9. The method of claim 1, wherein the material comprises a first material, and wherein said controlling the temperature of the material comprises placing a second material, the temperature of which is controlled, in contact with said first material.

10. The method of claim 9, wherein said controlling the temperature of the material comprises controlling the temperature of the second material to maintain the first material at a controlled temperature.

11. The method of claim 9, wherein said controlling the temperature comprises controlling the temperature of the first material without placing the first material or second material in a bath.

12. The method of claim 1, further comprising timing said directing of said series of acoustic pulses into the material, and timing receipt of echoes of said pulses used in said estimating.

13. The method of claim 1, further comprising receiving echoes of said pulses, wherein said estimating comprises applying one or more signal processing algorithms to every nth echo received, where "n" is a predefined integer.

14. The method of claim 1, wherein said pulses are sinusoids with a predetermined envelope.

15. The method of claim 1, wherein said displacement is measured directly.

16. The method of claim 1, wherein said measuring a displacement comprises measuring a displacement of the material over time to provide time-based data.

17. A method of evaluating the effectiveness of an anti-clotting treatment, said method comprising:
carrying out the steps of claim 1 prior to administration of the anti-clotting treatment, wherein the material comprises blood;
carrying out the steps of claim 1 at least one time after administration of the anti-clotting treatment; and
comparing results generated from each iteration of the steps of claim 1 to determine the effect of the anti-clotting treatment on the at least one physical characteristic of the blood.

18. A method of evaluating the effectiveness of an anti-clotting treatment, said method comprising:
carrying out the steps of claim 1 at least one time after administration of the anti-clotting treatment, wherein the material comprises blood; and
comparing results generated from each iteration of the steps of claim 1 to determine the effect of the anti-clotting treatment on the at least one physical characteristic of the blood.

19. A method of evaluating the effectiveness of a pro-clotting treatment provided to a patient to increase the ability of the patient's blood to clot, said method comprising:
carrying out the steps of claim 1 at least one time after administration of the pro-clotting treatment, wherein the material comprises blood; and
comparing results generated from each iteration of the steps of claim 1 to determine the effect of the pro-clotting treatment on the at least one physical characteristic of the blood.

20. A method of characterizing changes in at least one physical property of a biological material over time, said method comprising:
generating a series of acoustic pulses and directing said series of pulses into the material such that at least one of the pulses is of sufficiently high intensity to induce physical displacement of the material and wherein each of said acoustic pulses is of finite duration and of brief duration relative to a duration of said generating and said directing;
controlling a temperature of the material;
estimating at least one physical property of the material based on measuring a displacement resulting from said induced physical displacement of the material; and
repeating said generating and estimating steps after passage of a time interval.

21. The method of claim 20, wherein the material comprises soft tissue.

22. The method of claim 21, wherein the soft tissue comprises blood.

23. A method of characterizing at least one physical property of a material, said method comprising:
generating a series of acoustic pulses and directing said series of pulses into the material such that at least one of the pulses is of sufficiently high intensity to induce physical displacement of the material and wherein each of said acoustic pulses is of finite duration and of brief duration relative to a duration of said generating and said directing;
controlling the temperature of the material;
measuring a displacement, either directly or indirectly, of the material resulting from said induced physical displacement thereof, wherein said measuring comprises receiving optical reflections from the material as the material is being physically displaced; and
estimating at least one characteristic of the physical displacement based on said measuring, wherein said estimating is based on the optical reflections received.

24. A method of characterizing at least one physical property of a biological material, said method comprising:
generating a series of acoustic pulses and directing said series of pulses through skin of a subject, into the material such that at least one of the pulses is of sufficiently high intensity to induce physical displacement of the material and wherein each of said acoustic pulses is of finite duration and of brief duration relative to a duration of said generating and said directing;
measuring a displacement, either directly or indirectly, of the material resulting from said induced physical displacement thereof; and
estimating at least one characteristic of the physical displacement based on said measuring; and
repeating said generating, measuring and estimating steps after passage of a time interval.

25. The method of claim 24, wherein said measuring comprises receiving at least two of said acoustic pulses reflected from the material and said estimating is based on the acoustic pulses received.

26. The method of claim 24, wherein said measuring comprises receiving optical reflections from the material as the material is being physically displaced and said estimating is based on the optical reflections received.

27. The method of claim 24, wherein the material comprises soft tissue.

28. The method of claim 24, wherein the material comprises blood.

29. A method of characterizing a stage of development of a blood clot comprising carrying out the steps of claim 24, wherein the material comprises blood, and comparing the at least one estimated characteristic to previously generated data to gauge the stage of development of the blood clot.

30. A method of evaluating the effectiveness of an anti-clotting treatment, said method comprising:
   carrying out the steps of claim 24 prior to administration of the anti-clotting treatment, wherein the material comprises blood;
   carrying out the steps of claim 24 at least one time after administration of the anti-clotting treatment; and
   comparing results generated from each iteration of the steps of claim 24 to determine the effect of the anti-clotting treatment on the at least one physical characteristic of the blood.

31. A method of evaluating the effectiveness of an anti-clotting treatment, said method comprising:
   carrying out the steps of claim 24 at least one time after administration of the anti-clotting treatment, wherein the material comprises blood; and
   comparing results generated from each iteration of the steps of claim 24 to determine the effect of the anti-clotting treatment on the at least one physical characteristic of the blood.

32. A method of evaluating the effectiveness of a pro-clotting treatment provided to a patient to increase the ability of the patient's blood to clot, said method comprising:
   carrying out the steps of claim 24 at least one time after administration of the pro-clotting treatment, wherein the material comprises blood; and
   comparing results generated from each iteration of the steps of claim 24 to determine the effect of the pro-clotting treatment on the at least one physical characteristic of the blood.

33. A method of characterizing at least one physical property of a material, said method comprising:
   generating a series of acoustic pulses and directing said series of pulses into the material such that at least one of the pulses is of sufficiently high intensity to induce physical displacement of the material and wherein each of said acoustic pulses is of finite duration and of brief duration relative to a duration of said generating and said directing;
   receiving an echo of at least said at least one of the pulses of sufficiently high intensity to induce physical displacement of the material;
   applying a signal processing algorithm to a signal transduced from said received echo;
   estimating a displacement of the material; and
   repeating said generating, receiving, applying and estimating steps after passage of a time interval.

* * * * *